(12) United States Patent
List et al.

(10) Patent No.: US 11,446,436 B2
(45) Date of Patent: Sep. 20, 2022

(54) FLOW DETECTOR

(71) Applicant: Roche Diabetes Care, Inc., Indianapolis, IN (US)

(72) Inventors: Hans List, Oberzent (DE); Frederic Wehowski, Hockenheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 575 days.

(21) Appl. No.: 16/309,736

(22) PCT Filed: Jul. 6, 2017

(86) PCT No.: PCT/EP2017/066901
§ 371 (c)(1),
(2) Date: Dec. 13, 2018

(87) PCT Pub. No.: WO2018/007502
PCT Pub. Date: Jan. 11, 2018

(65) Prior Publication Data
US 2019/0184099 A1 Jun. 20, 2019

(30) Foreign Application Priority Data

Jul. 8, 2016 (EP) .................................... 16178656
Sep. 6, 2016 (EP) .................................... 16187465

(51) Int. Cl.
*A61M 5/168* (2006.01)
*A61M 5/172* (2006.01)
(Continued)

(52) U.S. Cl.
CPC ........ *A61M 5/16886* (2013.01); *A61M 5/142* (2013.01); *A61M 5/14244* (2013.01);
(Continued)

(58) Field of Classification Search
CPC ................ A61M 5/16886; A61M 5/44; A61M 2005/16868; A61M 2005/16872;
(Continued)

(56) References Cited

U.S. PATENT DOCUMENTS 6,280,408 B1 *  8/2001  Sipin ................... A61M 5/1483
                                                          604/65
6,813,944 B2   11/2004  Mayer et al.
(Continued)

FOREIGN PATENT DOCUMENTS

EP        1117802 B1    7/2001
EP      1 970 677 A1    9/2008
(Continued)

OTHER PUBLICATIONS

International Patent Application PCT/EP2017/066901 International Search Report dated Sep. 25, 2017, 3 pages.
(Continued)

*Primary Examiner* — Amber R Stiles
*Assistant Examiner* — Avery Smale
(74) *Attorney, Agent, or Firm* — Woodard, Emhardt, Henry, Reeves & Wagner, LLP

(57) ABSTRACT

Disclosed is a flow detector (1) for releasable coupling with a flow channel (20) in a channel coupling area and detecting a flow of liquid drug in the flow channel (20), the flow detector including: an upstream thermoelectric element (10*a*) and a downstream thermoelectric element (10*b*), wherein the upstream thermoelectric element (10*a*) and the downstream thermoelectric element (10*b*) are arranged spaced apart from each other and movable independent from each other; an upstream biasing element (15*a*) and a downstream biasing element (15*b*), wherein the upstream biasing element (15*a*) acts on the upstream thermoelectric element (10*a*), thereby biasing the upstream thermoelectric element
(Continued)

(10a) towards the channel coupling area, and the downstream biasing element (15b) acts on the downstream thermoelectric element (10b), thereby biasing the downstream thermoelectric element (10b) towards the channel coupling area independently from the upstream biasing element (15a).

16 Claims, 7 Drawing Sheets

(51) Int. Cl.
    *A61M 5/44* (2006.01)
    *A61M 5/142* (2006.01)
(52) U.S. Cl.
    CPC .... *A61M 5/14248* (2013.01); *A61M 5/16831* (2013.01); *A61M 5/172* (2013.01); *A61M 5/44* (2013.01); *A61M 2005/16868* (2013.01); *A61M 2005/16872* (2013.01); *A61M 2205/3334* (2013.01); *A61M 2205/3368* (2013.01)
(58) Field of Classification Search
    CPC ...... A61M 2205/3368; A61M 5/14244; A61M 5/172; A61M 2205/3334; A61M 5/168; A61M 5/16831; A61M 2005/16863; A61M 2205/3379; A61M 2205/3382; A61M 2205/3386; A61M 2205/3673
    See application file for complete search history.

(56) References Cited

U.S. PATENT DOCUMENTS

| | | | | |
|---|---|---|---|---|
| 2008/0257412 A1* | 10/2008 | Gordon | ............. | A61M 5/16877 137/8 |
| 2010/0049127 A1 | 2/2010 | Haueter | | |
| 2013/0237955 A1* | 9/2013 | Neta | ................. | A61M 5/16831 604/500 |
| 2014/0114238 A1 | 4/2014 | Lee et al. | | |
| 2014/0155867 A1* | 6/2014 | Lee | ......................... | G01F 1/684 604/533 |
| 2016/0175519 A9* | 6/2016 | Lee | ..................... | A61M 5/1452 604/67 |

FOREIGN PATENT DOCUMENTS

| | | |
|---|---|---|
| EP | 2 163 273 A1 | 3/2010 |
| EP | 2 361 646 A1 | 8/2011 |
| EP | 2 457 602 A1 | 5/2012 |
| EP | 2 510 960 A1 | 10/2012 |
| EP | 2 510 962 A1 | 10/2012 |
| EP | 2 753 380 A1 | 7/2014 |
| EP | 2 881 128 A1 | 6/2015 |
| ER | 2 696 915 A1 | 2/2014 |
| WO | WO 2009/114115 A1 | 9/2009 |
| WO | WO 2012/059209 A1 | 5/2012 |
| WO | WO 2012/069308 A1 | 5/2012 |
| WO | WO 2012/140063 A1 | 10/2012 |
| WO | WO 2013/029999 A1 | 3/2013 |
| WO | WO 2013/034159 A1 | 3/2013 |

OTHER PUBLICATIONS

Stachowiak, H. et al., "A thermoelectric sensor for fluid flow measurement, principles, calibration and solution for self temperature compensation." Flow Measurement and Instrumentation 9 (1998) 135-141. 8 pages.

* cited by examiner

FLOW DETECTOR

REFERENCE TO RELATED APPLICATIONS

This application is a national stage of International Patent Application Number PCT/EP2017/066901, filed Jul. 6, 2017. International Patent Application Number PCT/EP2017/066901 claims the benefit of European Patent Application Number 16187465.6, filed Sep. 6, 2016. International Patent Application Number PCT/EP2017/066901 further claims the benefit of European Patent Application Number 16178656.1, filed Jul. 8, 2016.

TECHNICAL FIELD

The present disclosure lies in the field of ambulatory infusion systems and ambulatory infusion devices, as used in a number of therapies, in particular diabetes therapy. More particularly, the disclosure lies in the field of flow detectors and flow detection methods.

BACKGROUND AND PRIOR ART

Continuous subcutaneous insulin infusion (CSII) is an established state-of the art therapy of diabetes mellitus. It is carried out via sophisticated computer-controlled ambulatory infusion devices that are commercially available from a number of suppliers. Traditionally, such ambulatory infusion devices are realized as miniaturized syringe driver devices and are worn, e.g., in a trousers' pocket, with a belt clip, or the like. Recently, alternative devices have been developed that are directly attached to the patient's skin. Also alternative fluidic designs have been proposed, e.g. downstream dosing architectures with a variable intermediate dosing cylinder, as disclosed, e.g., in EP1970677A1. While diabetes therapy is a major field of application of ambulatory infusion devices, they may also be used in further therapies, such as cancer therapy and pain therapy.

While substantive improvements have been made over the years regarding many aspects, supervising the administration is still an issue of concern. In particular, liquid drugs such as insulin may occasionally and under adverse circumstances clog the infusion tubing or infusion cannula, resulting in an occlusion. According to the state of the art, occlusions are detected indirectly, e.g. by measuring and evaluating a reaction force in the drive chain, which significantly and continuously increases in case of an occlusion. However, since the overall system elasticity is low but still present, and because the typical drug administration rates according to a basal delivery schedule may be very low, in particular for children and juveniles, and further in view of large uncertainties that result, e.g., from a variable piston friction in syringe-driver systems, the delay time until an occlusion is detected may be significantly and in the range of many hours and potentially up to a day or more. At the same time, false alarms are cumbersome and should be voided as far as possible.

SUMMARY OF DISCLOSURE

In view of this situation, it has been proposed to directly measure the liquid drug flow. Thermal flow sensors that may be used for this purpose typically include a heating element and two temperature sensors that are arranged upstream respectively downstream from the heating element, with the heating element and the temperature sensors being thermal coupled to the liquid. For the liquid being in rest (i.e. now flow being present), thermal energy that is emitted from the heating element is thermally conducted by the liquid to both temperature sensors which accordingly measure an identical heat increase (assuming a symmetrical setup). If, however, a liquid flow is present from "upstream" towards "downstream", the thermal energy is largely transported downstream, resulting in the downstream temperature sensor measuring a higher temperature as compared to the upstream temperature sensor, with the temperature difference being indicative for the liquid velocity.

In principle, such thermal flow sensor may be suited for monitoring the operation of an ambulatory infusion system as explained before. It has to be considered, however, that all liquid-contacting elements need to be sterile and further need to be realized as disposables with a limited lifetime of a few days up to, e.g., two weeks. Ideally, the flow sensor would accordingly also be designed as sterile disposable. For a number of reasons related to handling, manufacture and in particular costs, however, such approach is undesirable and largely unfeasible.

When providing the heating element and the temperature sensors as part of the ambulatory infusion device with a releasable coupling to a flow channel, e.g. a piece of tubing, however, a good thermal coupling with, e.g., the tubing walls is hard to achieve.

The WO2012/059209 discloses a thermal flow sensor of the above-mentioned type, where the heating element and the temperature sensors are arranged as standard surface-mounted components on a spring-loaded suspension that is pressed against a tubing wall with a contact force. Due to the very limited space in ambulatory infusion devices, however, some amount of curvature or bending is typically present in the tubing, resulting in an at least partly insufficient thermal coupling. Small flow rates respectively an administration of small liquid drug volumes are therefore impossible to detect.

The U.S. Pat. No. 6,813,944 discloses an alternative design where the heating element and the temperature sensors are implemented on a common piece of semiconductor substrate to which the flow channel directly couples. While this approach is advantageous from a thermal point of view, it requires a separation between the (disposable) flow channel and the (durable) flow sensor as part of an infusion device directly at the semiconductor, such that the semiconductor and its tiny bonding wires are freely accessible and unprotected whenever the disposable flow channel is exchanged. Such setup is accordingly unfeasible from a practical and handling point of view.

It is an overall objective of the present disclosure to improve the situation regarding the use of thermal flow detectors or flow sensors for monitoring or supervising the liquid drug administration by an ambulatory infusion system. Favorably, disadvantages of the prior art as discussed before are reduced or avoided.

A further overall objective of the present disclosure is to reduce the number of components of a thermal flow sensor for the before-discussed use. Reducing the number of components is generally favourable from a cost point of view and is particularly advantageous with respect to the required installation space, which is a particularly critical aspect in the context of ambulatory infusion systems.

The overall objectives are achieved by the subject matter of the independent claims, with favorable and exemplary embodiments being defined by the dependent claims as well as the overall disclosure.

When referring, in the context of the present document, to a liquid drug, such liquid drug may in particular be a liquid insulin formulation. It may, however, also be any other liquid drug that may be administered via an ambulatory infusion system, such as pain killers or cancer drugs.

According to an aspect, the objective is achieved by a flow detector for releasable coupling with a flow channel in a channel coupling area and detecting a flow of liquid drug in the flow channel. The flow detector includes an upstream thermoelectric element and a downstream thermoelectric element. The upstream thermoelectric element and the downstream thermoelectric element are arranged spaced apart from each and movable independent from each other. The upstream thermoelectric element and the downstream thermoelectric element are in particular arranged spaced apart from each other along an extension direction of the flow channel in an operational configuration. The extension direction of the flow channel corresponds to the axis of the liquid drug flow direction. The first and downstream thermoelectric element are in particular movable in a direction traverse to the extension direction of the flow channel, i.e. towards and away from the flow channel and may be movable only traverse to the extension direction of the flow channel. The corresponding movements of the thermoelectric elements may be pivoting, bending, or flexing movements, but also, e.g. linear displacement movements. The thermoelectric elements are movable relative to the flow channel which is generally fixed in an operational configuration.

The flow detector may further include an upstream biasing element and a downstream biasing element. The upstream biasing element acts on the upstream thermoelectric element, thereby biasing the upstream thermoelectric element towards the channel coupling area. The downstream biasing element acts on the downstream thermoelectric element, thereby biasing the downstream thermoelectric element towards the channel coupling area independently from the upstream biasing element. The biasing forces correspond to the contact forces between the thermoelectric elements and the flow channel.

The channel coupling area is an area where, in an operational configuration, the first thermoelectric area and the downstream thermoelectric element contact the flow channel. The channel coupling area generally extends along the—typically, but not necessarily—linear extension of the flow channel. The phrase "operational configuration" refers to a configuration as present during use where the flow detector, in particular via its thermoelectric elements, is coupled to a flow channel in the channel coupling area. In an operational configuration, the upstream thermoelectric element couples to the flow channel at an upstream position and the downstream thermoelectric element couples to the flow channel in a downstream position. A biasing of a thermoelectric element towards the channel coupling area is equivalent to a biasing towards the flow channel in an operational configuration.

The downstream thermoelectric element being biased towards the channel coupling area respectively the flow channel independently from the upstream thermoelectric element also means that the first biasing element and the second biasing element are functionally independent from each other. The upstream biasing element accordingly exerts an upstream biasing force onto the upstream thermoelectric element and the downstream biasing element independently exerts a downstream biasing force onto the downstream thermoelectric element.

The biasing forces are the contact forces by which the thermoelectric elements are pressed against a wall of the flow channel and are generally oriented traverse to the flow channel, thereby ensuring the required thermal coupling between the flow channel and the thermoelectric elements. For the desirable good thermal coupling, the contact forces should be high. Since the cross sectional area of the flow channel, however is typically small, the contact forces need to be sufficiently low not to significantly deform the flow channel. Such deformation of the flow channel, resulting in a reduction of the cross section, is likely to cause occlusions and further cause shear forces that result in a number of drugs, such as insulin, to degrade.

The individual biasing of the thermoelectric elements towards the flow channel reduces the tolerance requirements and is in particular suited in designs where some degree of curvature is present for the flow channel in the area of the flow detector. Such situation is typical and in fact hardly avoidable for an ambulatory infusion device that is carried substantially continuously night and day and for which small dimensions, i.e. a slim design and a small footprint, are of major importance.

Generally, it is desirable to position the thermoelectric elements of a thermal flow detector or flow sensor spaced apart from each other, but as close to each other as possible along the flow channel. Arranging the thermoelectric components to be separately movable and providing separate biasing elements, however, requires additional space and may therefore be considered as little advantageous. It is found, however, that this disadvantage is more than outbalanced by the improved thermal coupling that may be achieved.

In the context of an ambulatory infusion system, the flow direction of the liquid drug is generally known, resulting of "upstream" and "downstream" being well defined. For a reversed flow direction, however, the role of "upstream" and "downstream" elements (such as thermoelectric elements and biasing elements) is simply reversed. In a general sense, the terms "upstream" and "downstream" may be read as "first" and "second", resulting in a wording independent from the flow direction.

In the context of the present document, the "flow channel" means a duct that is, during operation, filled with liquid drug over its total cross sectional area and is further surrounded by a wall or an arrangement of walls along its whole circumference. The coupling of the flow channel with the thermoelectric elements is accordingly a thermal and mechanical coupling with an outer wall surface of the flow channel. Typically, the flow channel is a length of tubing of usually circular cross section. Other designs of the flow channel, however, are possible as well. The flow channel may in particular be realized by a groove or depression in a substantially rigid and e.g. injection-moulded component. At its open side, the groove or channel is covered by a foil. The thickness of such foil may be in a typical range of 20 Micrometres to 200 Micrometres. For such design, the thermoelectric elements contact, in an operational configuration, the foil of the flow channel. This type of design is particularly suited in the context of thermal flow detection or flow measurement because the thermal transfer resistance is typically considerably lower as compared to tubing.

The flow channel is typically a part of a one-way fluidic device that is coupled to an ambulatory infusion device for a limited application time of typically a number of days up to, e.g., two weeks, via corresponding mating couplers as discussed further below in more detail. Therefore, the phrase "releasable" coupling refers, in the context of the present document, to a coupling that is, after being established, e.g. by a user, self-maintaining and may be released without damaging the flow detector or an ambulatory infusion device of which the flow detector may be part of. Furthermore, the releasable coupling allows a sequential coupling of the flow detector with a number of flow channels respectively of an ambulatory infusion device with a number of fluidic one-way components in sequence. The arrangement is such that the thermoelectric elements contact the flow channel in the channel coupling area.

A flow detector in accordance with the here as well as further below-described types may be designed and operated to quantitatively measure a flow rate or flow velocity of liquid drug within the flow channel. As will be discussed in more detail further below, however, it may also be operated in a binary way to indicate whether or not a flow of liquid (above a threshold and/or within a given range) occurs at a specific point in time or within a specific time window. Therefore, a flow detector in accordance with the present disclosure may, in some embodiments, not be sufficiently accurate for a quantitative measurement. Furthermore, the signals that are provided by the flow detector may, in some embodiments, be evaluated in a qualitative and in particular binary way, rather than quantitatively.

In an embodiment, the upstream thermoelectric element and the downstream thermoelectric element are surface mounted components.

In an embodiment, the downstream thermoelectric element is configured to operates as downstream temperature sensor and senses a downstream temperature at the downstream position. The upstream thermoelectric element may be configured to operate as heating element, thereby heating liquid inside the flow channel at the upstream position, and to operate as upstream temperature sensor and sense an upstream temperature at the upstream position. This type of embodiment is discussed further below in more detail in the context of another aspect of the present disclosure.

In an embodiment, the flow detector further includes a middle thermoelectric element. The middle thermoelectric element is arranged between and spaced apart from the upstream thermoelectric element and the downstream thermoelectric element. The middle thermoelectric element is movable independent from the upstream thermoelectric element and the downstream thermoelectric element. A flow detector according to this type of embodiment may further comprise a middle biasing element. The middle biasing element acts on the middle thermoelectric element, thereby biasing the middle thermoelectric element towards the channel coupling area with a middle biasing force independent from the upstream biasing element and the downstream biasing element. In an operational configuration, the middle thermoelectric element couples to the flow channel in a middle position.

Such embodiment with a middle thermoelectric element corresponds, regarding the thermoelectric elements, to a classic design for a thermal flow detector or flow sensor. Here, the middle thermoelectric element is generally a heating element, typically in form of an electric resistor, while the upstream respectively downstream thermoelectric element is an upstream respectively downstream temperature sensor. The arrangement is favorably symmetric, with the upstream thermoelectric element and the downstream thermoelectric element being of identical design and arranged equally spaced apart from the middle thermoelectric element.

As will become more readily apparent in the following, the arrangement of the middle thermoelectric element is generally the same as it is the case for the upstream thermoelectric element and the downstream thermoelectric element. Embodiments and characteristics that are in the following discussed in more detail for the upstream and downstream thermoelectric element, such as the way of arrangement on a carrier and the way of coupling to the flow channel, also hold true for the middle thermoelectric element in an analogue way.

According to a further aspect, the overall objective is achieved by a further type of flow detector for releasable coupling with a flow channel in a channel coupling area and detecting a flow of liquid drug in the flow channel. The flow detector includes an upstream thermoelectric element and a downstream thermoelectric element. The upstream thermoelectric element and the downstream thermoelectric element are arranged spaced apart from each other. The upstream thermoelectric element is arranged to couple to the flow channel in a channel coupling area at an upstream position and the downstream thermoelectric element is arranged to couple to the flow channel in the channel coupling area at a downstream position, such that the downstream thermoelectric element operates as downstream temperature sensor and senses a downstream temperature at the downstream position. This type of flow detector may further include a flow detector control unit. The upstream thermoelectric element of this type of flow detector is configured to operate as heating element, thereby heating liquid inside the flow channel at the upstream position, and to operate as upstream temperature sensor and sense an upstream temperature at the upstream position.

This type of flow detector is based on the same fundamental principle as a classic flow detector or flow sensor design with separate heating element, upstream temperature sensor and downstream temperature sensor. In contrast to the classic design, however, the upstream thermoelectric element serves a double purpose as both heating element and upstream temperature sensor, thereby sparing the dedicated heating element. Such arrangement is found to be sufficient and well-suited in particular in applications where the required measurement precision is limited or binary signal evaluation as explained before is sufficient.

This type of embodiment may be configured such that the upstream thermoelectric element is operated and in particular supplied with electric power in the same way when operated as heating element and upstream temperature sensor. The upstream thermoelectric element may be continuously supplied with electrical power during heating and temperature measurement, resulting in the heating being continued during temperature measurement. Alternatively, the upstream thermoelectric element may be operated differently for operating as heating element and subsequently operating as upstream thermoelectric element. The upstream thermoelectric energy may in particular powered with higher power (in particular supply voltage and/or supply current) when operated as heating element as compared to operating as upstream temperature sensor, thus favorably enabling a shortened heating time. Powering of the upstream thermoelectric element may for example be controlled via a switched power supply with pulse-width modulation (PWM).

In an embodiment of this type of flow detector, the upstream thermoelectric element and downstream thermoelectric element are movable independent from each other. The flow detector may further include an upstream biasing element and a downstream biasing element. The upstream biasing element acts on the upstream thermoelectric element, thereby biasing the upstream thermoelectric element towards the channel coupling area respectively the flow channel as explained before. The downstream biasing element acts on the downstream thermoelectric element, thereby biasing the downstream thermoelectric element towards the channel coupling area respectively the flow channel independently from the upstream biasing element.

In an embodiment, the upstream thermoelectric element is arranged on an upstream element carrier and the downstream thermoelectric element is arranged on a downstream element carrier, and a gap is present between the upstream element carrier and the downstream element carrier. The gap has a gap width along the extension direction of the flow channel in an operational configuration.

Providing the upstream thermoelectric element and the downstream thermoelectric element on different carriers with a gap in between is counter-intuitive in so far as the gap adds to the distance between the thermoelectric elements along the flow channel, which is generally unfavorable. A common carrier, e.g. a common printed circuit board, however, forms a thermal bridge between the thermoelectric elements, resulting in a considerable portion of the heat transfer between the thermoelectric elements occurring via the carrier, rather than the flow channel respectively the liquid within the flow channel, as desired. A gap between the thermoelectric elements, in contrast, increases the thermal insulation because of the low thermal conductivity of the (air) gap, thus enhancing the thermal coupling between thermoelectric elements and flow channel. This favorable effect is found to outweigh the generally negative influence of the increased distance.

In an embodiment with a middle thermoelectric element, the middle thermoelectric element may be arranged on a middle element carrier, and an upstream gap may be present between the upstream element carrier and the middle element carrier along the extension direction of the flow channel, and a downstream gap may be present between the middle element carrier and the downstream element carrier along the extension direction of the flow channel. The setup may be symmetric with the gaps having the same width.

In an embodiment, the upstream thermoelectric element is arranged on an upstream flexible printed circuit board element and the downstream thermoelectric element is mounted on a downstream flexible printed circuit board element.

In such embodiment, the upstream respectively downstream printed circuit board element serve, in addition to carrying the thermoelectric elements, as movable elements for the movable arrangement of the thermoelectric elements. The flexible printed circuit board elements may have an elongated "finger-shaped" design and extend traverse to the flow channel, thereby allowing flexing traverse to the flow channel, resulting in a movement of the thermoelectric elements towards respectively away from the flow channel, traverse to the flow direction respectively extension of the flow channel. For such an arrangement, the flexible printed circuit board elements generally have a flexing area which enable pivoting movement of the thermoelectric elements towards and away from the flow channel respectively the channel coupling area.

In an embodiment with a middle thermoelectric element, the middle thermoelectric element may be arranged on a middle flexible circuit board element in an analogue way.

Typically, the flexible printed circuit board elements extend parallel to each other and maintain their parallel arrangement when flexing. Alternatively, however, the flexible printed circuit board elements may be angled relative to each other. The flexible circuit board elements may be separate from each other and separately attached to a support structure, e.g. a rigid printed circuit board. In a particular embodiment, however, the flexible printed circuit board elements extend from a common flexible printed circuit board base that may be formed integrally with the flexible circuit board elements.

In an embodiment, the upstream thermoelectric element is arranged on a side of the upstream flexible circuit board element pointing away from the channel coupling area and the downstream thermoelectric element is arranged on a side of the downstream flexible circuit board element pointing away from the channel coupling area. For an embodiment with a middle thermoelectric element, the middle thermoelectric element may, for this type of embodiment, be arranged on a side of the middle flexible printed circuit board element pointing away from the channel coupling area. Thermoelectric elements pointing towards respectively away from the channel coupling area implies that, in an operational configuration, they point towards respectively away from the flow channel, when viewed from the corresponding carrier, e.g. flexible printed circuit board element.

In alternative embodiments, the upstream thermoelectric element, the downstream thermoelectric element and an optional middle thermoelectric element may each be arranged on a side of the corresponding printed circuit board element pointing towards the flow channel. For this type of embodiment, the thermoelectric elements couple directly to the flow channel respectively a wall of the flow channel. In this regard, such arrangement corresponds to a classic thermal flow sensor design. Here the heat exchange between the thermoelectric elements and the flow channel occurs via the housing of the thermoelectric elements.

For an embodiment where the thermoelectric elements are arranged on the sides of the flexible printed circuit board elements pointing away from the flow channel, the flexible printed circuit board elements are, in an operational configuration, situated between the thermoelectric elements and the flow channel, such that the upstream respectively downstream thermoelectric element couples with the flow channel indirectly via the corresponding flexible printed circuit board, rather than directly. Such arrangement is counter-intuitive in that the indirect coupling in principle downgrades the thermal coupling. However, the primary direction of thermal energy flow from respectively towards the thermoelectric elements is given by the direction of lowest thermal resistance. In dependence of the specific design, the lowest thermal resistance is typically present between the electric contacts respectively contact pads of the thermoelectric elements and the corresponding (typically copper) conductor paths on the flexible printed circuit board elements. This particularly holds true for surface mounted devices (SMDs) respectively surface mounted elements. A majority of thermal energy transfer is accordingly via the conductor paths. For an arrangement of the proposed type with the thermoelectric elements being arranged on the sides of the flexible printed circuit board elements pointing away from the flow channel, the flexible printed circuit board elements contact the flow channel and the conductor paths are available for the thermal energy transfer. Thereby, improved thermal coupling may be achieved event if the thermal energy exchange is via the backing material of the flexible printed circuit board elements with comparatively high thermal resistance.

In an embodiment, the flow detector includes a positioning structure, the positioning structure being designed to position the flow channel with respect to the upstream thermoelectric element and the downstream thermoelectric element. In embodiments with a middle thermoelectric element, the positioning structure is further designed to position the flow channel with respect to the middle thermoelectric element. The positioning is such that the upstream thermoelectric element, the downstream thermoelectric element and optionally the middle thermoelectric element contact, in an operational configuration, the flow channel at the corresponding upstream position, downstream position and middle position, respectively. Via the positioning structure, the position and extension direction of the flow channel in the channel coupling area is defined in relation to the thermoelectric elements.

The positioning structure may be designed to directly contact and guide the flow channel. In such embodiment, the positioning structure may, e.g., be realized by a grove-carrying element, wherein the groove is designed to receive the flow channel that is formed, e.g. by a length of tubing. The upstream thermoelectric element, the downstream thermoelectric element and optionally the middle thermoelectric element contact the flow channel in the channel coupling area as explained before.

In an embedment where the flow channel is part of a fluidic device with a well-defined geometric arrangement, the positioning structure may be or include a mating coupler, in particular a fluidic device coupler, that is designed to mate with a corresponding counter mating coupler, in particular an infusion device coupler of the fluidic device such that the flow channel is correctly positioned. Optionally, the positioning structure may also serve as abutment that absorbs the biasing forces that are exerted by first biasing element, second biasing element and optional third biasing element.

In an embodiment, the upstream thermoelectric element and the downstream thermoelectric element are thermistors, in particular negative temperature coefficient (NTC) thermistors. NTCs are widely available at low costs and show particularly favorable characteristics for flow detectors in accordance with the present disclosure. Alternatively, however, other types of thermoelectric elements may be used, e.g. PN junction semiconductors.

In an embodiment, the upstream thermoelectric element and the downstream thermoelectric element are NTC thermistors of different electric resistance. This arrangement results in an asymmetric electrical design which may be generally used but is particularly favorable in combination with a specially designed evaluation unit as explained below. Alternatively, however, the upstream thermoelectric element and the downstream thermoelectric element may have identical characteristics and be, e.g., NTCs of identical nominal electric resistance and temperature coefficient.

In an embodiment, the flow detector further includes a first reference thermoelectric element and a second reference thermoelectric element. The first reference thermoelectric element and the second reference thermoelectric element are arranged such that they are thermal isolated respectively decoupled, i.e. do not thermal couple to the flow channel in an operational configuration. For this purpose, the first reference thermoelectric element and the second reference thermoelectric element may in particular be arranged somewhat remote respectively spaced part from the upstream and downstream thermoelectric element and the channel coupling area.

The first reference thermoelectric element and the second reference thermoelectric element are arranged such that their mutual thermal coupling corresponds to the mutual thermal coupling between the upstream thermoelectric element and the downstream thermoelectric element if no flow is present in the flow channel. Favorably, the first reference thermoelectric element is of the same type as the upstream thermoelectric element and the second reference thermoelectric element is of the same type as the downstream thermoelectric element.

In embodiments where the flow detector comprises an additional middle thermoelectric element, a third reference thermoelectric element may be present and arranged between the first reference thermoelectric element and the second reference thermoelectric element in an analogue way to the arrangement of the middle thermoelectric element between the upstream thermoelectric element and the downstream thermoelectric element.

An embodiment with reference thermoelectric elements is favourable in the context of the administration of small liquid amounts and larger quantities as well. Especially the arrangement with just two thermoelectric elements is very sensitive to fast changes of flow in the flow channel. If the changes are slow, the detection becomes the more insufficient the slower the changes are. The reference thermoelectric elements are exposed to the same environmental conditions, and in particular the same temperature and temperature variations as the upstream and downstream and downstream thermoelectric elements.

An evaluation unit as discussed further below in more detail may process the signals provided by the first reference thermoelectric element and the second reference thermoelectric element in the same ways as the signals provided by the upstream thermoelectric element and the downstream thermoelectric element respectively. One of the evaluation units (associated respectively operatively coupled with the upstream thermoelectric element and the downstream thermoelectric element) provides a flow-dependent output signal, while the other evaluation unit (associated respectively operatively coupled with the first reference thermoelectric element and the second thermoelectric element) provides a flow-independent reference output signal, which, however, reflects and is influenced by other influence factors, in particular the temperature, in the same way as the flow-dependent output signal. The two signals may be fed into and further processed by an compensation unit which is designed to determine and evaluate a relation, in particular a difference or deviation, between the flow-dependent output signal and the reference output signal as measure for the liquid flow in the flow channel. A combination of the two evaluation units and the compensation unit is also referred to as evaluation and compensation unit. As explained before, the compensation unit compensates for the undesired influence of distortion factors such as changes in temperature.

In an embodiment of an evaluation and compensation unit, the evaluation of compensation unit is designed, in a first mode of operation, to only process the signal provided by the upstream thermoelectric element and the downstream thermoelectric element. In the first mode of operation, only the evaluation unit that is associated with the upstream thermoelectric element and the downstream thermoelectric element may be active, providing the flow-dependent output signal. This type of evaluation and compensation unit is further designed, in an alternative second mode of operation, to additionally process a signal that is provided by the first reference thermoelectric element and the second reference thermoelectric element, and to determine and evaluate a relation between the flow-dependent output signal and the reference output signal as explained before. The evaluation and compensation unit is favorably configured to operate in the first mode of operation or alternatively in the second mode of operation in dependence of a liquid volume that is administered and/or in dependence of a duration of liquid drug flow in the flow channel.

The evaluation and compensation unit may be configured to operate in the first mode of operation for the administration of small liquid drug volumes, e.g. smaller than a pre-determined volume threshold, and to operate in the second mode of operation for larger liquid drug volumes, e.g. above the pre-determined volume threshold. Additionally considering the flow-independent reference output signal is favourable in this case because the administration of larger volumes can be associated with a comparatively slow and creeping change of the flow-dependent output signal caused by a cumulative occlusion, resulting in the end of the liquid flow being hard to detect.

In an embodiment, the flow detector includes an evaluation unit, wherein the evaluation unit is designed to provide an output signal of variable frequency. The frequency depends on a difference between the upstream temperature as sensed by the upstream thermoelectric element and the downstream temperature as sensed by the downstream thermoelectric element. As will be explained in more detail further below in the context of exemplary embodiments, such evaluation unit may be implemented in a particularly compact way with a small number of components, based, e.g., on a typical microcontroller according to the state of the art. This type of embodiment may especially be realized based on a Schmitt-Trigger, an oscillator, e.g. an RC oscillator, and a reference voltage supply, wherein the upper and lower threshold of the Schmitt-trigger are determined by the resistance of the upstream thermoelectric element and the downstream thermoelectric element, respectively.

According to a still further aspect, the overall objective is achieved by an ambulatory infusion device. The ambulatory infusion device includes a fluidic device coupler. The fluidic device coupler is designed for releasable mating coupling, in an operational configuration, with an infusion device coupler of a fluidic device with a flow channel. The ambulatory infusion device further includes a pump drive unit, configured to administer liquid drug out of a drug container to a patient's body via the flow channel. The ambulatory infusion device further includes a pump control unit, configured to control operation of the pump drive unit for continuous drug administration according to a time-variable basal infusion administration rate. The ambulatory infusion pump further includes a flow detector in operative coupling with the pump control unit. The flow detector is a flow detector in accordance with the disclosure of the present document. In an operational state, the ambulatory infusion device, the fluidic device and a drug container form a common compact unit.

The pump drive unit and the pump control unit favorably form, in combination with a drug container and/or the fluidic device, a metering pump that is designed for the administration of liquid drug, in particular insulin, in well-defined doses.

In some embodiments, the pump drive unit includes a spindle drive that is designed to couple with a piston of a—typically, but not necessarily cylindrical—drug cartridge as drug container, such that the piston is displaced inside the drug cartridge in well-defined incremental steps in a syringe-like way. Here, the pump drive unit typically includes a rotatory motor as actuator, a reduction gear, a drive nut and a threaded lead screw in operative engagement with the drive nut, the lead screw being designed for coupling with the piston.

Alternatively, the pump drive unit may include the drive nut but not the lead screw which may be permanently coupled to the piston. Instead of a simple lead screw, more advanced arrangements, such as a telescopic drive rod may be used. Syringe-driver pumps are well known for ambulatory infusion devices in a variety of design variants and typically used in state-of-the art systems.

Alternatively, the pump drive unit may be designed to operatively couple to and cooperate with another type of pump unit, such as micro membrane pump or a downstream-dosing unit as disclosed, e.g. in EP1970677A1, EP1970677A1, EP2510962, EP2510960, EP2696915, EP2457602, WO2012/069308, WO2013/029999, EP2753380, EP2163273, and EP2361646. Syringe-driver pumps and downstream-dosing units as mentioned before are examples of positive-displacement metering pumps with a well-defined and design-given relation between pump actuator or pump drive movement and drug administration.

The pump drive unit is favorably designed for the administration of single doses in a range of 1 microliter or below, for example 500 nanoliters, 200 nanoliters, or 100 nanoliters. For the typical concentration U100 for liquid insulin formulations, 1 milliliter of liquid contain 100 International Units (IUs) of insulin.

The ambulatory infusion pump is favorably designed for the metered administration independent form an output signal that is provided by the flow detector, with the flow detector serving for administration monitoring and supervision purposes. This condition is fulfilled for positive-displacement respectively volumetric metering pumps, such as syringe-driver pumps or pumps with a down-stream dosing unit as mentioned before.

The fluidic device is designed to fluidic couple to the drug container and establish a connection with a patient interface, such as an infusion cannula respectively an infusion tubing directly via a fluidic patient interface coupler, or may directly include the patient interface. In some embodiments, the fluidic device is directly formed integral with the drug container, e.g. a drug cartridge. In embodiments where the pump includes, in an operational state, further fluidic units, such as membrane pump or a downstream dosing unit as explained before, such fluidic units may be part of the fluidic device as well. In any case, the fluidic device includes, between the outlets of the drug container the patient interface respectively patient interface coupler, the flow channel that is arranged to releasable couple with the flow detector in the channel coupling area.

The fluidic device and the ambulatory infusion device are designed for releasable mating coupling via a fluidic device coupler and a infusion pump device coupler, which may be realized by latches, catches, snap-fit couplers bayonet couplers, or the like. The ambulatory infusion device and the fluidic device may be further designed such that, in an operational configuration, the fluidic device is fully or partly received by a fluidic device compartment of an ambulatory infusion device housing. In an operational configuration, the channel coupling area is typically located inside the ambulatory infusion device housing.

The flow channel is, at least in the channel coupling area, arranged along a straight line that corresponds as defined by its extension direction and is arranged such that it is contacted by the thermoelectric elements in a configuration where the fluidic device and the ambulatory infusion device are coupled. In an embodiment, the fluidic device includes a plate-shaped abutment element which supports the e.g. tubular flow channel and absorbs the biasing forces as mentioned before. The flow channel may be arranged in a groove of the abutment element and protrude above the surface to allow contacting. Alternatively, positioning elements such as positioning pins, positioning posts or the like may be provided that project from the abutment element along the extension direction for positioning the flow channel. Alternatively to a tubular flow channel, the flow channel may, as mentioned before, be directly realized as groove or the like and covered by a foil as discussed before. For the here-discussed types of embodiment, the correct alignment and positioning between the flow channel and the thermoelectric elements relies on the fluidic device coupler of the ambulatory infusion device and the ambulatory infusion device coupler of the fluidic device as positioning structure. Alternatively, the flow channel may be movably arranged in the fluidic device and a positioning structure may be realized as part of the ambulatory infusion device.

In an embodiment, the pump control unit is configured to control the pump unit to administer drug pulses of pre-set pulse volume and to vary a time between consecutive pulses in dependence of a required basal administration rate, wherein the flow detector is configured to be intermittently operated for the administration of the drug pulses. Alternatively or additionally, the pump control unit may be configured for the administration of drug pulses of variable pulse volume with a constant or variable time between consecutive drug pulses. The control unit may further be configured to control additional the administration of drug boli of adjustable bolus volume on demand.

According to a further aspect, the overall objective is achieved by an ambulatory infusion system, the ambulatory infusion system including ambulatory infusion device and a fluidic device as discussed above and/or further below.

According to a still further aspect, the overall objective is achieved by a medical assembly, the medical assembly including a flow sensor and a fluidic device or a flow channel as discussed above and/or further below.

An ambulatory infusion device and an ambulatory infusion system in accordance with the present disclosure may be designed to be carried by a user and to operate for an extended time period of a number of days up to a number of weeks continuously and concealed from view, e.g. in a trousers pocket, with a belt clip or the like. Alternatively, the ambulatory infusion device or ambulatory infusion system may be designed to be directly attached to a user's skin, e.g. via an adhesive pad, for the extended time period. An ambulatory infusion device and an ambulatory infusion system in accordance with the present disclosure are designed to operate and administer liquid drug independent from an orientation with respect to gravity.

According to a still further aspect, the overall objective is achieved by a method for releasable coupling a flow sensor with a flow channel for detecting a flow of liquid drug in the flow channel. The method includes releasable coupling an upstream thermoelectric element and a downstream thermoelectric element with the flow channel. The upstream thermoelectric element and the downstream thermoelectric element are arranged spaced apart from each other along an extension direction of the flow channel and movable independent from each other. The upstream thermoelectric element and the downstream thermoelectric element are in particular movable traverse to the extension direction of the flow channel. The method further includes biasing the upstream thermoelectric element towards the flow channel, and independently biasing the downstream thermoelectric element towards the flow channel.

Optionally, the method may include releasable coupling a middle thermoelectric element with the flow channel. The middle thermoelectric element is arranged between and spaced apart from the upstream thermoelectric element and the downstream thermoelectric element and is independently movable. The method may further include independently biasing the middle thermoelectric element towards the flow channel.

According to a still further aspect, the overall objective is achieved by a method for detecting liquid drug flow in a flow channel. The method includes releasable coupling an upstream thermoelectric element with the flow channel, wherein the upstream thermoelectric element and the downstream thermoelectric element are arranged spaced apart from each other along an extension direction of the flow channel. The upstream thermoelectric element couples to the flow channel at an upstream position and the downstream thermoelectric element couples to the wall of the flow channel at a downstream position. The method further includes controlling the downstream thermoelectric element to operate as downstream temperature sensor and sense a downstream temperature at the downstream position. The method further includes controlling the upstream thermoelectric element to operate as heating element, thereby heating liquid inside the flow channel at the upstream position, and to operate as upstream temperature sensor and sense an upstream temperature at the upstream position. The method further includes processing signals provided by the upstream thermoelectric element and the downstream thermoelectric element, thereby detecting a liquid drug flow in the flow channel.

The upstream thermoelectric element, the downstream thermoelectric element and the optional middle thermoelectric element releasable couple to the flow channel in a channel coupling area as explained before.

In an embodiment, the method includes determining, via the flow detector, whether or not a drug pulse is administered at a pre-determined point in time or in a pre-determined time window in accordance with an administration regime.

In a further embodiment, the method includes determining, via the flow detector, whether a number of drug pulses, in particular a number of consecutive drug pulses is not administered at a number of corresponding pre-determined points in time or pre-determined time windows.

In an embodiment, the method includes generating an alarm if a drug pulse or a number of consecutive drug pulses is not administered.

In an embodiment, the method includes providing a first reference thermoelectric element and a second reference thermoelectric element. The first reference thermoelectric element and the second reference thermoelectric element are arranged in a thermal isolated manner with respect to the upstream thermoelectric element and the downstream thermoelectric element, and further spaced apart from the channel coupling area. For this type of embodiment, the method includes determining a flow-dependent output signal by processing a signal provided by the upstream thermoelectric element and the downstream thermoelectric element. The method further includes independently determining a flow-independent reference output signal by processing a signal provided by the first reference thermoelectric element and the second reference thermoelectric element. The method further includes evaluating a relation between the flow-dependent output signal and the reference output signal.

In an embodiment, the method includes determining and processing the flow-dependent output signal only or alternatively both the flow-dependent output signal and the reference output signal, in dependence of a liquid volume that is administered and/or in dependence of a duration of liquid drug flow in the flow channel.

Methods in accordance with the present disclosure may be carried out by devices, in particular flow detectors and/or ambulatory infusion devices, in accordance with the present disclosure. Specific embodiments of disclosed devices, in particular flow detectors and/or ambulatory infusion devices disclose, at the same time corresponding method embodiments. In the same way, specific embodiments of disclosed methods disclose, at the same time, corresponding devices, in particular flow detectors and ambulatory infusion devices.

WAYS OF CARRYING OUT THE INVENTION

Figure 1:
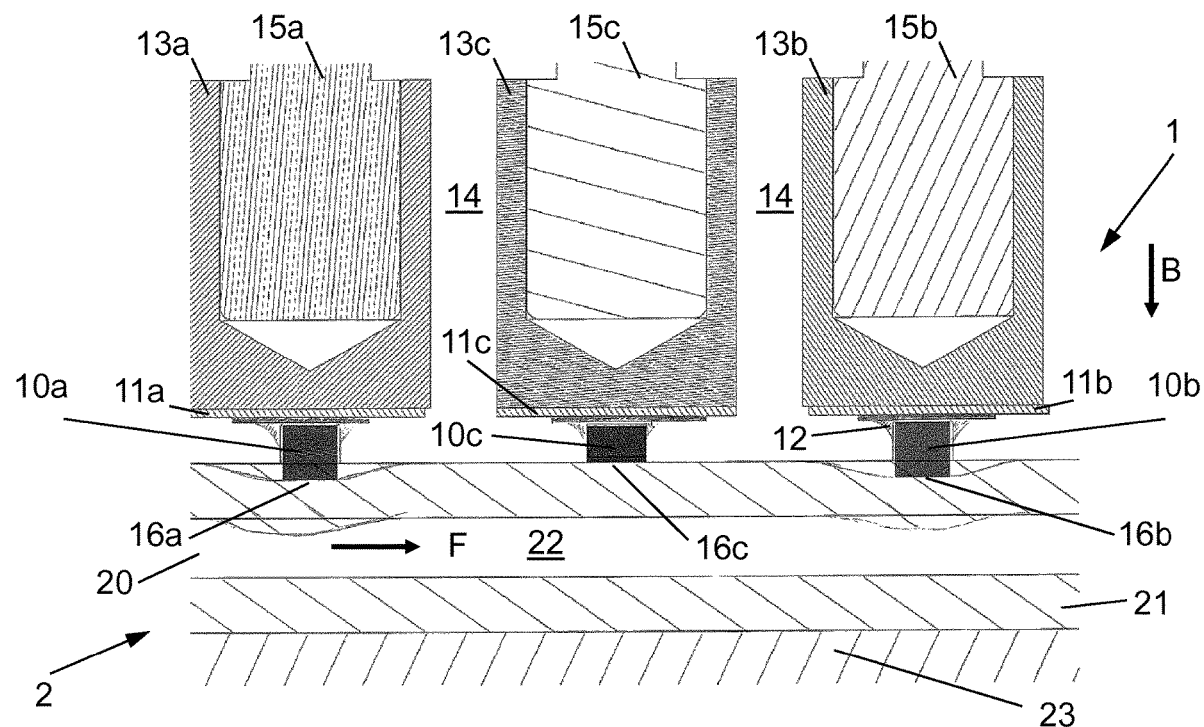
FIG. 1 shows an embodiment of a flow detector in operative coupling with a flow channel in a schematic side view.

In the following, reference is first made to FIG. 1, showing an exemplary embodiment of a flow detector 1 and a fluidic device 2 in a schematic structural view.

For the sake of clarity, elements that are present in different figures and/or embodiments are not necessarily referenced separately in each and every figure.

The flow detector 1 includes an upstream thermoelectric element 10a, a downstream thermoelectric element 10b, and an optional middle thermoelectric element 10c. In this example, the upstream thermoelectric element 10a and the downstream thermoelectric element 10b are NTC thermistors of identical characteristics, while the middle thermoelectric element 10c is a heating element (resistor). In an embodiment without the middle thermoelectric element 10c, the upstream thermoelectric element 10a and the downstream thermoelectric element 10b are NTC thermistors of favorably different characteristics, in particular different resistance.

The thermoelectric elements 10a, 10b, 10c are surface mounted elements or surface mounted devices (SMDs), each of them being mounted on a corresponding separate element carrier 11a, 11b, 11c in form of flexible circuit board elements. The thermoelectric elements 10a, 10b, 10c are mounted on and connected to the corresponding printed circuit board elements 11a, 11b, 11c via soldering joints 12 (typically two soldering joints 12 for each of the thermoelectric elements 10a, 10b, 10c).

On the opposite side of the printed circuit board elements 11a, 11b, 11c, corresponding insulator elements 13a, 13b, 13c are arranged. Each of the insulator elements 13a, 13b, 13c has a central blind bore in which an end section of a corresponding biasing element 15a, 15b, 15c is arranged. The biasing element 15a is the upstream biasing element, the biasing element 15b the downstream spring element and the biasing element 15c the middle biasing element of the flow detector 1. The opposite ends of the biasing elements 15a, 15b, 15c are supported by a support structure (not shown) that may be part of an ambulatory infusion device housing. The biasing elements 15a, 15b, 15c are exemplarily realized as coil springs. The biasing elements 15a, 15b, 15c each separately exert a biasing force onto the corresponding carrier element 11a, 11b 11c and the thermoelectric elements 10a, 10b, 10c in direction B.

The upstream element carrier 11a and the middle element carrier 11c, as well as the middle element carrier 11c and the downstream element carrier 11b are pairwise separated by a gap 14 of identical width.

The fluidic device 2 includes the flow channel 20 with a hollow lumen 22 of circular cross section that is circumferentially surrounded by a flow channel wall 21, in combination forming a tubular structure. Other types of flow channels may be used as well.

At a side adjacent to the flow detector 1 respectively the thermoelectric elements 10a, 10b, 10c, the fluidic device 2 includes a plate-shaped abutment element 23 that supports the flow channel 20 and absorbs the contact forces respectively biasing forces. The flow channel exemplarily extends along a straight line with the flow direction being indicated by F.

The upstream thermoelectric element 10a contacts the flow channel 20 at an upstream position (16b) where the elastic flow channel wall 21 is accordingly slightly deformed under the influence of the contact force respectively biasing force. The same holds true for the downstream thermoelectric element 10b that contacts the flow channel 20 at a downstream position 16b and the middle thermoelectric element 10c that contacts the flow channel 20 at the middle position 16c (not shown for the middle thermoelectric element 10c for clarity reasons). The area of the upstream contact position 16a, the downstream contact position 16b, and the middle contact position 16c, in combination, forms the channel coupling area.

Figure 2:
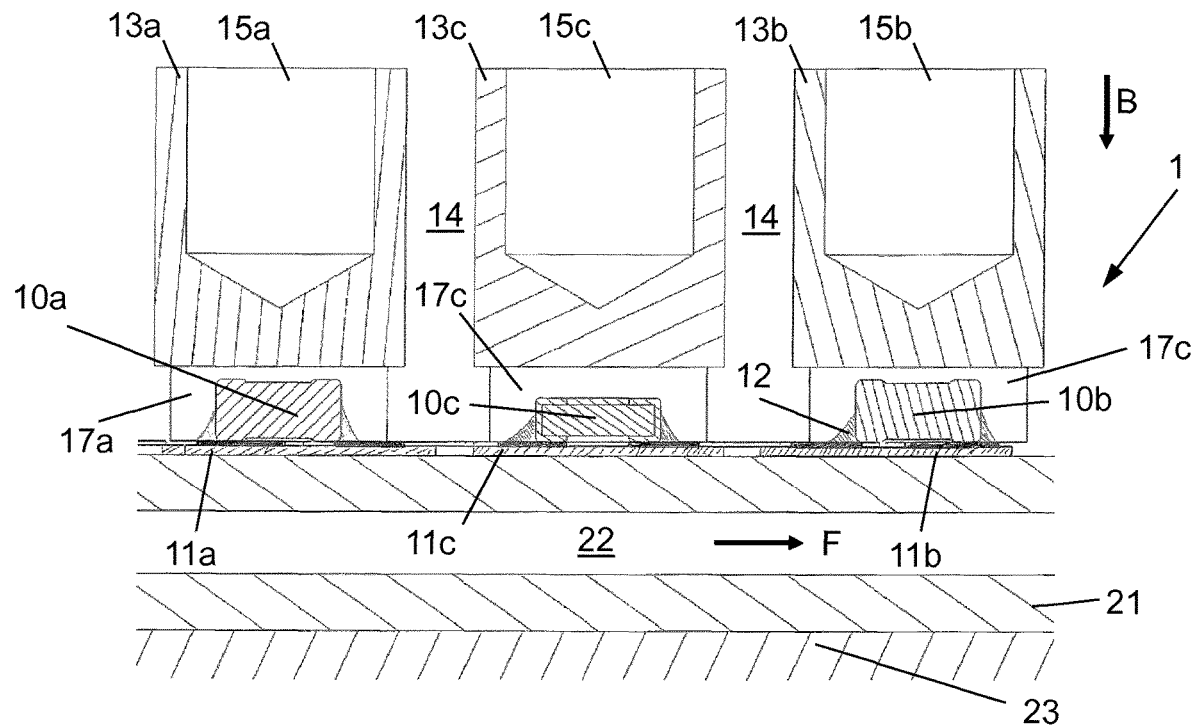
FIG. 2 shows a further embodiment of a flow detector in operative coupling with a flow channel in a schematic side view.

In the following, reference is additionally made to FIG. 2, showing a further exemplary embodiment of the flow detector 1 together with components of a fluidic device 2. In a number of aspects, the embodiment of FIG. 2 is identical to the before-discussed embodiment of FIG. 1. The following discussion is focused on the differences.

In the embodiment of FIG. 1, the thermoelectric elements 10a, 10b, 10c are arranged on the side of the carrier elements (flexible printed circuit board elements 11a, 11b, 11c) that face the flow channel 20 and the channel coupling area. The thermoelectric elements 10a, 10b, 10c accordingly directly contact the flow channel 20 respectively the flow channel wall 21. In the embodiment of FIG. 2, in contrast, the thermoelectric elements 10a, 10b 10c are arranged on the corresponding carrier elements 11a, 11b, 11c on a side pointing away from the flow channel 20 and the channel coupling area, but pointing towards the biasing elements 15a, 15b, 15c instead.

The thermoelectric elements 10a, 10b, 10c accordingly contact the flow channel 20 indirectly, via the carrier elements 11a, 11b, 11c, rather than directly. The result is a further improvement of the thermal coupling, as explained before in the general description. Additionally, it can be seen that the channel coupling area between the carrier elements 11a, 11b, 11c and the flow channel 20 is larger as compared to the thermoelectric elements 10a, 10b, 10c. The deformation of the flow channel wall 21 is accordingly favourably reduced or even avoided.

In order to improve the desired thermal isolation between the thermoelectric elements and the (typically metallic) biasing elements, an optional insulator cap 17a, 17b, 17c is provided in this embodiment for each of the thermoelectric element and the corresponding insulator 13a, 13b, 13c and biasing element 15a, 15b, 15c, thus preventing a direct contact between the thermoelectric elements 10a, 10b, 10c and the insulators 13a, 13b, 13c on the one side and the biasing elements 15a, 15b, 15c on the other side. The insulator caps 17a, 17b, 17c are made from a material of low thermal conductivity, typically plastics, and put over the thermoelectric elements 10a, 10b, 10c. The insulator caps 17a, 17b, 17c may, e.g., be glued onto the carrier elements 11a, 11b, 11c after soldering of the thermoelectric elements 10a, 10b, 10c. The insulator caps 17a, 17b, 17c may in principle also be realized integral with the insulators 13a, 13b, 13c.

Figure 3:
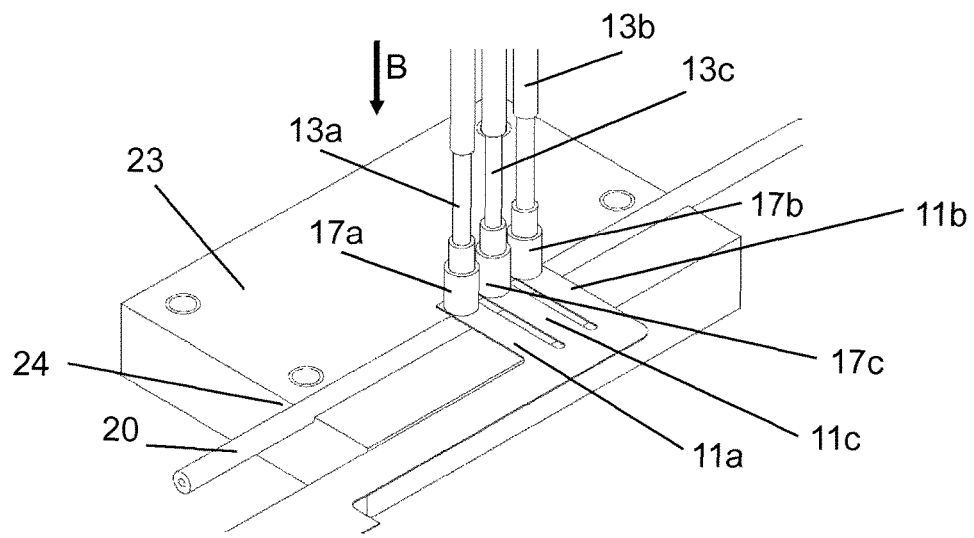
FIG. 3 shows the embodiment of FIG. 2 in a schematic three-dimensional view.

In the following, reference is additionally made to FIG. 3, showing the arrangement form FIG. 2 in a perspective view. It can be seen that the carrier elements (flexible printed circuit board elements) 11a, 11b, 11c are finger-shaped and extend parallel from a common flexible printed circuit board 11d, traverse to the extension direction of the flow channel 20. It can further be seen that flow channel 20 is partly arranged in a groove 24 of the abutment element 23, the groove 24 positioning the flow channel 20 relative to the flow detector 1, thereby serving as positioning structure. A corresponding arrangement may also be used in the embodiment of FIG. 1.

FIG. 1 to FIG. 3 show embodiments with three separate thermoelectric elements where a middle thermoelectric element 10c as heating element is distinct from the upstream and downstream thermoelectric elements 10a, 10b as temperature sensors. Embodiments where the upstream thermoelectric element 10a serves as both heating element and as upstream temperature sensor may be realized in the same way, omitting, however, the middle thermoelectric element 10c and associated components.

Figure 4:
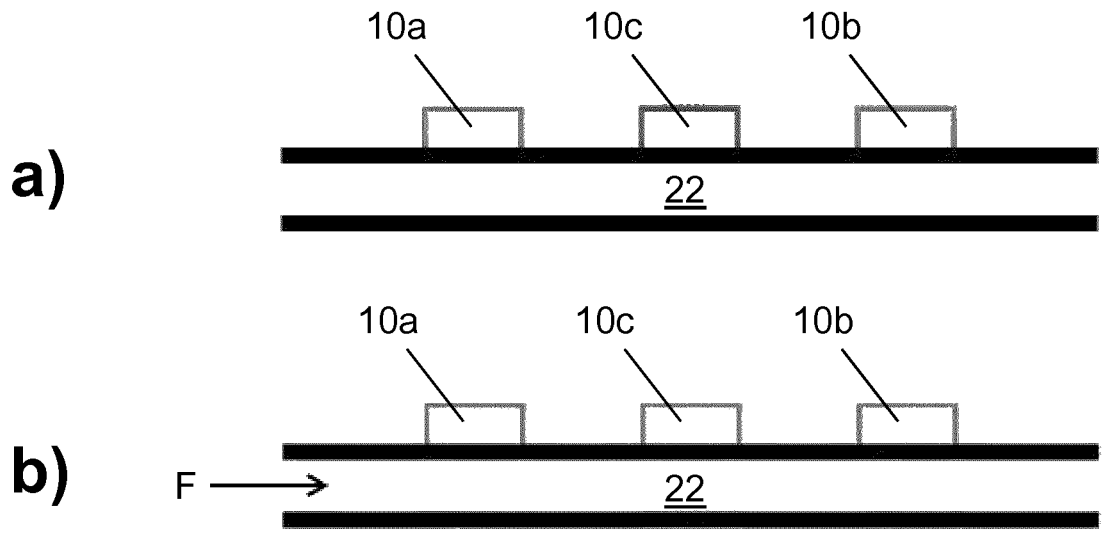
FIG. 4 illustrates the operation of an embodiment of a flow detector.

In the following, reference is additionally made to FIGS. 4a, 4b, illustrating the operation of an embodiment of a flow detector with three thermoelectric elements. FIG. 4a shows the situation shortly before a drug pulse is administered. Both the upstream thermoelectric element 10a as upstream temperature sensor and the downstream thermoelectric element 10b as downstream temperature sensor are at a low base temperature that corresponds to a temperature that can be measured in a static state without liquid flow in the lumen 22. The middle thermoelectric element 10c as heating element heats the liquid in its proximity to an increased temperature. Without liquid flow, the heat would be transported equally into the upstream direction (against the flow direction F) and the downstream direction (with the flow direction F) via thermal conduction, resulting in substantially equal temperatures at the upstream thermoelectric element 10a and the downstream thermoelectric element 10b.

FIG. 4b illustrates the situation shortly after switching off the heating via middle thermoelectric element 10c and administering a drug pulse. Now, the heat is transported with the drug in the lumen 22 in the flow direction F, resulting in the downstream thermoelectric element 10b as downstream temperature sensor being at a higher temperature than the upstream thermoelectric element 10a as upstream temperature sensor. The measured temperature difference between the downstream thermoelectric element 10b and the upstream thermoelectric element 10a is evaluated in order to determining whether or not a liquid flow has actually occurred. Optionally, the heating may be continued during the measurement.

Figure 5:
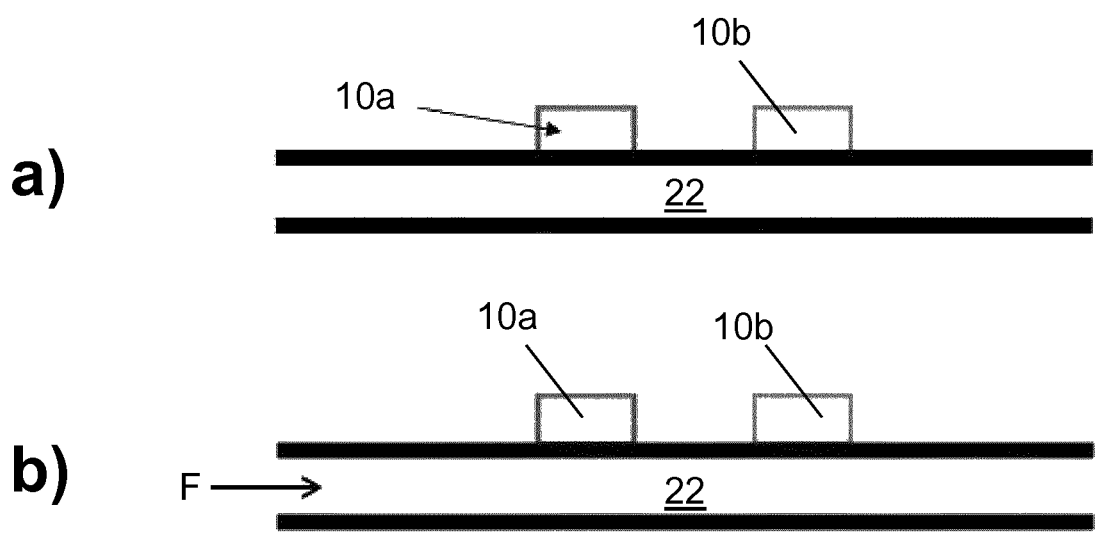
FIG. 5 illustrates the operation of a further embodiment of a flow detector.

FIGS. 5a, 5b show situations corresponding to FIGS. 4a, 4b for an embodiment with only two thermoelectric elements, where the upstream thermoelectric element 10a serves as both heating element and upstream temperature sensor, and the downstream thermoelectric element 10b serves as downstream temperature sensor. In FIG. 5a, the upstream thermoelectric element 10a is operated as heating element that heats the liquid in its proximity to an increased temperature, while the downstream thermoelectric element 10b is at a lower temperature. As discussed further below in the context of FIG. 6 in more detail, the upstream thermoelectric element 10a heats the liquid continuously or substantially continuously, resulting in the upstream thermoelectric element 10a being at a higher temperature than the downstream thermoelectric element 10b. Since, however, heated liquid drug is, in FIG. 5b, transported towards the downstream thermoelectric element 10b and replaced by colder liquid from upstream of the flow detector, the temperature at the upstream thermoelectric element 10a will be somewhat decreased and the temperature at the downstream thermoelectric element 10b will be somewhat increased. The temperature difference between the upstream thermoelectric element 10a and the downstream thermoelectric element 10b is accordingly reduced because of the liquid drug flow.

Figure 6:
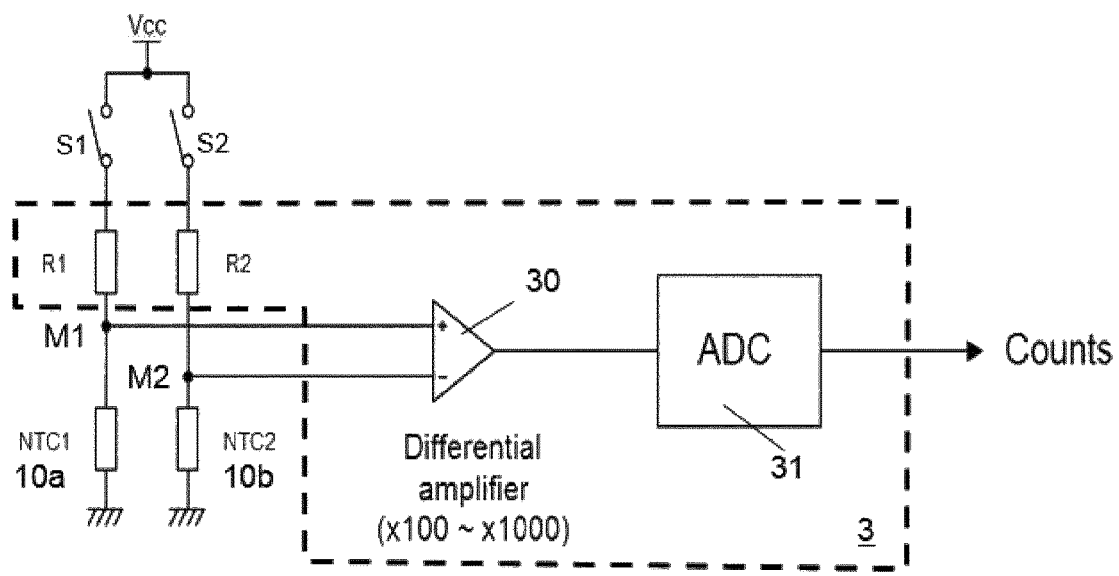
FIG. 6 shows an embodiment of the coupling of a flow detector with an evaluation unit.

In the following, reference is additionally made to FIG. 6, illustrating an embodiment of an evaluation unit 3 in interaction with the thermoelectric elements 10a, 10b. In this embodiment, the upstream thermoelectric element 10a and the downstream thermoelectric element 10b are NTCs (also referred to as NTC1 and NTC2) of exemplary identical characteristics and are arranged in series with corresponding fixed resistors R1 and R2 such that fixed resistor R1 and NCT1 respectively fixed resistor R2 and NTC2 each form a branch of a Wheatstone bridge that is selectively connectable to a voltage supply Vcc via switches S1 S2 that are closed for operation and otherwise open. The differential voltage between the midpoints M1, M2 of the two branches is fed to a differential amplifier 30 that is typically realized based on an operational amplifier (op-amp). The output of the differential amplifier 30 is fed into an analogue-to-digital converter (ADC) 31, the output of which (referenced as "counts" is) is accordingly dependent on and favourably substantially proportional to the temperature difference between NTC1 and NTC2.

The upstream thermoelectric element 10a (NTC1) may serve as both heating element and upstream temperature sensor with switch S1 being closed. After a heating period, switch S2 is additionally closed and the downstream thermoelectric element 10b (NTC2) is additionally powered for measuring the temperature difference. During the preceding heating time, switch S2 is opened in order to prevent NTC2 from heating the liquid at the downstream position. If no flow detection is carried out, both S1 and S2 are favourably open in order to save energy and avoid an unnecessary and generally unfavourable liquid heating.

In particular in embodiments of the above-described type where the first thermoelectric element 10a and the second thermoelectric element 10b are of identical characteristics and the upstream thermoelectric element 10a additionally serves as heating element, the downstream thermoelectric element 10b is only powered for a short period of time (typically in the range of some milliseconds) for the temperature measurement and is in particular not powered during the preceding heating time, as it would otherwise heat the liquid in the same way as the upstream thermoelectric element.

In a variant (not shown), a branch with a further switch and a further resistor in serial arrangement (like resistor R1 and switch S1) is provided in parallel to resistor R1 and switch S1, such that NTC1 may be powered alternatively via the further switch and the further resistor. The further resistor is favourably considerably smaller as compared to the resistor R1 and NTC1 is powered for the heating time via the further switch and further resistor, resulting in a favourable shortened heating time. The heating may be controlled by operating the further switch via pulse-width modulation. For the subsequent temperature difference measurement, the further switch is opened and switches S1, S2 are closed as explained before.

In a further variant, both the upstream thermoelectric element 10a (NTC1) and the downstream thermoelectric element 10b (NTC2) serve as temperature sensors only and an additional middle thermoelectric element is provided as dedicated heating element.

Figure 7:
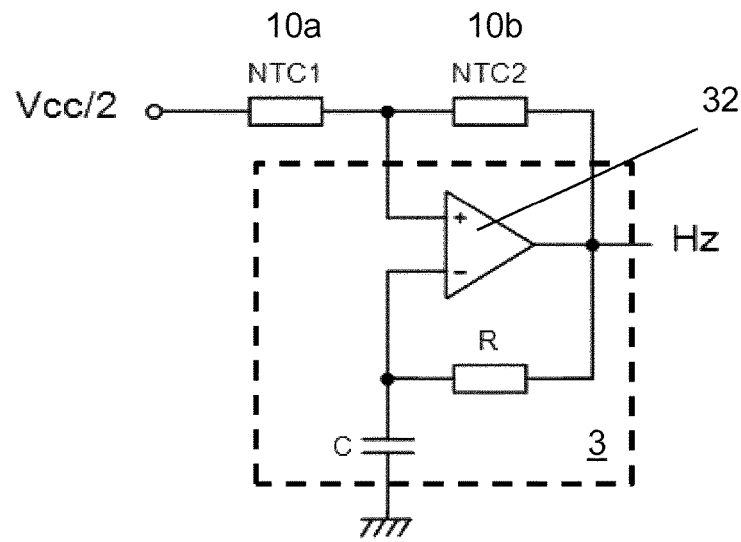
FIG. 7 shows the coupling of a flow detector with an evaluation unit according to a further embodiment.

In the following, reference is additionally made to FIG. 7, illustrating a further embodiment of an evaluation unit 3 in interaction with the thermoelectric elements 10a, 10b. This type of embodiment is particularly favourable if the upstream thermoelectric element 10a serves as both upstream temperature sensor and as heating element, and the upstream thermoelectric element 10a and the downstream thermoelectric element 10b are NTCs of different characteristics, in particular different resistance. The resistance of the upstream thermoelectric element 10a is considerably lower than the resistance of the downstream thermoelectric element 10b in order to prevent the downstream thermoelectric element 10b from heating the liquid in the same way as the upstream thermoelectric element 10a. Favorably, the resistance ration may be about 1:10 or more.

In the embodiment of FIG. 7, an e.g. op-amp-based comparator 32 forms, together with the thermoelectric elements NTC1, NTC2, a Schmitt-Trigger, the two thresholds of which are determined by the resistances of NTC1 respectively NTC2. Further, an oscillator of given frequency is present and coupled to the comparator 32. The oscillator is exemplarily realized as simple R-C oscillator with a frequency of, e.g. some Kilohertz (kHz) to some Megahertz (MHz). As a result, the output of the comparator 32 provides a square signal, the frequency of which depends on the temperature difference between NTC1 and NTCs and can be measured in a straight forward way.

Modern microcontrollers typically include components such as comparators, reference voltage supplies, timers and highly accurate crystal oscillators. Based on such a microcontroller, an evaluation unit 3 according to FIG. 7 may be realized with a very small number of further components (the resistor R, the capacitor C, and the NTCs as thermoelectric elements), thus providing a very compact and cost-efficient solution.

The evaluation unit 3, e.g. according to FIG. 6 or FIG. 7, may be realized partly or fully integral further functional units or circuitry, e.g. a pump control unit of an ambulatory infusion device.

Figure 8:
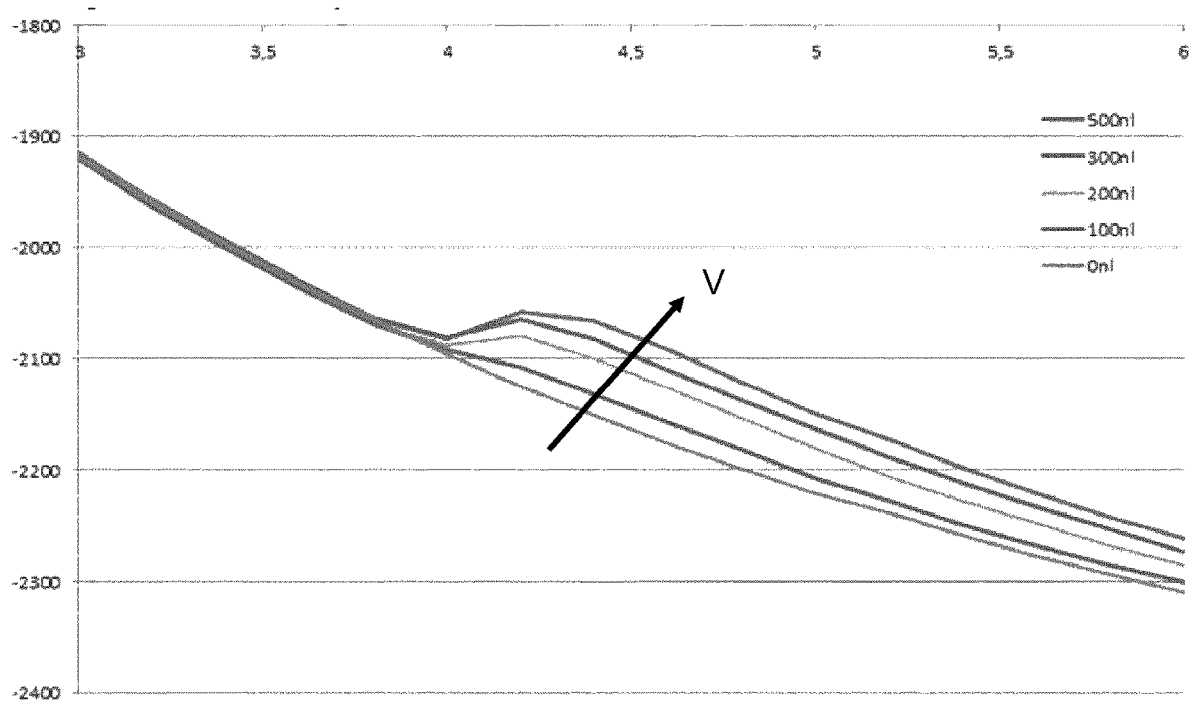
FIG. 8 shows the output of an evaluation unit for different drug pulse volumes.

In the following, reference is additionally made to FIG. 8. FIG. 8 shows exemplary measurement results as obtained in a flow detection element with a thermal flow detector 1 in accordance with FIG. 5 and an evaluation unit based on a Wheaton bridge as shown in FIG. 6.

The diagrams show the output of the ADC 31 (vertical axis) as a function of time (horizontal axis), with an increasing absolute value of the (exemplarily negative) ADC output corresponding to an increased temperature difference.

In the flow detection element, the upstream thermoelectric element 10a started operating as heating element at t=1 sec (not visible), and a drug pulse was administered at t=4 sec. The experiment was carried out with drug pulse volumes V of 100, 200, 300, 500 nl (nano litres), with 0 nl (i.e. no drug pulse is administered) being shown additionally as reference.

It can be seen that before the drug pulse is administered, all curves are substantially equal, indicating good reproducibility. The temperature difference between the upstream thermoelectric element 10a and the downstream thermoelectric element 10b increases over time in the shown period because of the heating, which decreases the resistance of the upstream thermoelectric element 10a due to its negative temperature coefficient. Also the potential of M1 (see FIG. 6) accordingly decreases.

The administration of the drug pulse results in a temporary and relatively sudden decrease of the temperature difference, resulting from the cooling effect caused by heated liquid being replaced by cooler downstream liquid at upstream thermoelectric element 10a and from the heating effect caused by cooler liquid being replaced by heated liquid at downstream thermoelectric element 10b. It can be seen that the effect increases with the drug pulse volume V. Subsequent to the administration of the drug pulse, the temperature difference again approaches the reference curve. All curves for the different drug pulse volumes V clearly distinguished from both the reference curve and each other and in particular drug pulses 200 nl or more are clearly distinguished. The evaluation may be carried out by evaluating the slope of the temperature difference versus time curve.

It is noted that in the flow detection experiment as illustrated in FIG. 8, heating was continuously carried out by powering the upstream thermoelectric element 10a (NTC1) over the duration of the experiment, while the downstream thermoelectric element 10b (NTC2) was powered by switching S2 only periodically for few milliseconds for temperature measurement, with a frequency of e.g. 10 Hz or less. In a practical application, heating would typically be stopped after the drug administration, e.g. at t=4.5 sec. This is also the time when the temperature difference may be evaluated.

Figure 9:
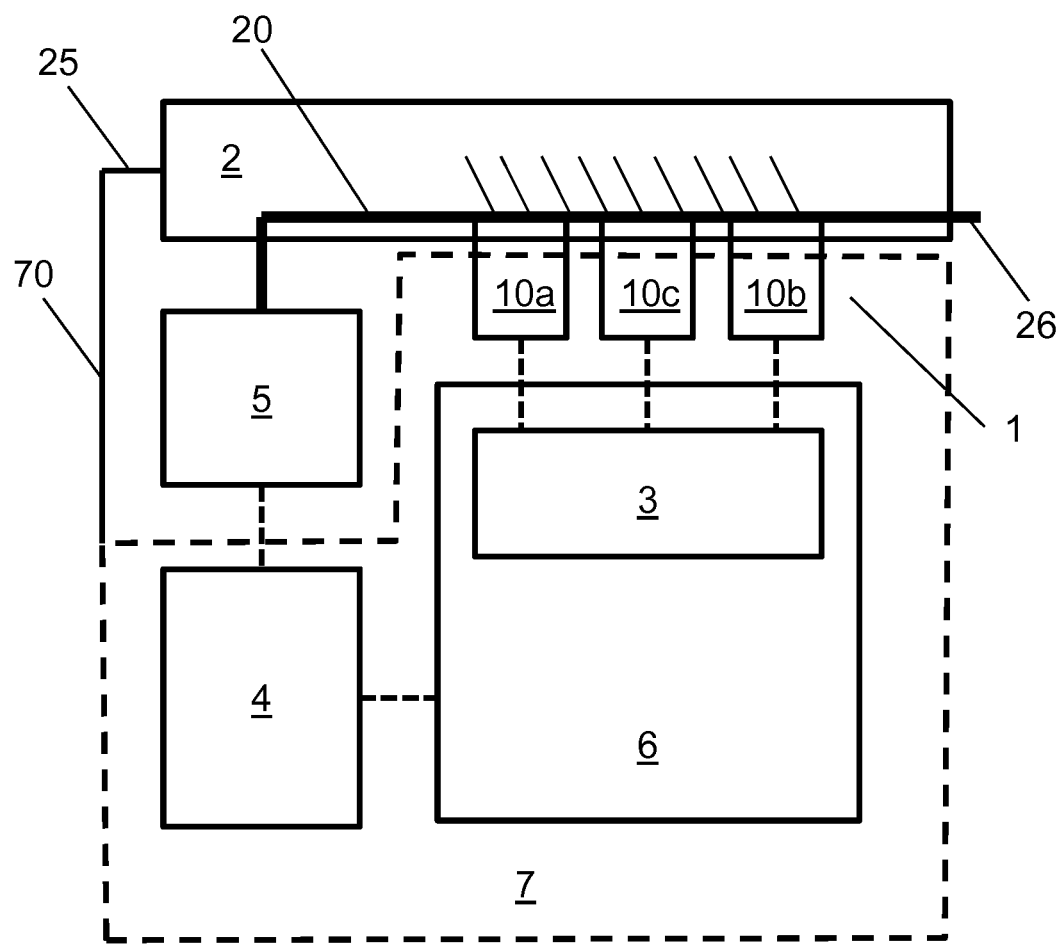
FIG. 9 shows an embodiment of an ambulatory infusion system in a schematic functional view.

In the following, reference is additionally made to FIG. 9, illustrating major components and functional units of an ambulatory infusion system in a schematic functional view.

In an operational state, the ambulatory infusion system includes an ambulatory infusion device 7, a drug container 5, and a fluidic device 2. The drug container 5 is exemplarily assumed to be a cylindrical cartridge that receives a sealing and displaceable piston, such that displacement of the piston along a longitudinal cartridge axis results in a corresponding displacement of liquid drug out of the container.

The ambulatory infusion device 7 includes a pump drive unit 4 in operative mechanical coupling with the drug container 5. For the before-mentioned type of drug container, the pump drive unit 4 may a spindle drive in releasable engagement with the piston, as generally known in the art, thus forming a syringe driver arrangement.

The ambulatory infusion device 7 further includes an electronic pump control unit 6 that is operatively coupled with the pump drive unit for controlling operation of the pump drive unit 4. The pump control unit 6 is favourably configured to control the pump drive unit 4 for the administration of drug boli of desired volume on demand and further for a basal drug administration according with an infusion rate according to a time-variable schedule. With respect to basal administration, individual drug pulses may be administered in fixed time intervals, e.g. every three minutes, with the drug pulse volume depending on the infusion rate. In particular for small infusion rates, basal delivery may also be carried out with a fixed pulse volume in a range of, e.g. 200 nano litres to 1 micro litre, and the time interval between consecutive pulses is adjusted in accordance with the desired rate. The evaluation unit 3 is exemplarily shown as part of the pump control unit 6 and may be realized integral with the general electronics circuitry of the ambulatory infusion pump 7. The evaluation unit 3 may, e.g. be designed according to FIG. 6 or FIG. 7.

The fluidic device 2 comprises an infusion device coupler 25 and the ambulatory infusion device 7 comprises a fluidic device coupler 70 that are designed for releasable mating coupling and are realized, e.g. as snap-fit coupling, bayonet coupling, or the like. In a coupled and operational state, both a mechanical coupling is provided as well as a fluidic coupling between the drug container 5 and the flow channel 20. Further in a coupled state, the flow channel 20 couples with thermoelectric elements 10a, 10b, 10c as explained before. The thermoelectric elements 10a, 10b, 10c are, like the overall flow detector, part of the ambulatory infusion device 7. A fluidic outlet 26 of the flow channel 20 is, in application, in fluidic coupling with an infusion site of the patient. For this purpose, the fluidic outlet may releasable couple with an infusion tubing, or include an infusion tubing or directly an infusion cannula. All of such designs are generally known in the art.

The flow detector 1 may be designed according to any embodiment in accordance with the present document, for example according to embodiments as shown in FIG. 1, FIG. 2, and FIG. 3. In FIG. 9, only the thermoelectric elements 10a, 10b, 10c are shown in interaction with the flow channel 20 for clarity reasons. It is noted that the flow detector 1 may, as discussed before, also comprise the upstream thermoelectric element 10a and the downstream thermoplastic element 10b, omitting the middle thermoelectric element 10c.

The drug container shown is shown separately from the ambulatory infusion pump 7 and the fluidic device 2 in FIG. 9 for illustrative purposes. In practice, it may, e.g., be received inside a container receptacle a housing of the ambulatory infusion pump 7. It may also be integral with the fluidic device 2. Further alternative fluidic designs may be used instead of an ordinary syringe-driver design. In particular, the fluidic device 2 may include respectively be realized as downstream dosing unit as mentioned before and disclosed, e.g. in EP1970677A1. Also, the drug container 5 is not necessarily realized as cylindrical cartridge but may also be, e.g., a flexible or semi-rigid pouch, as generally known in the art. Independent form the system design and the specific fluidic architecture, the ambulatory infusion pump 7, the drug container 5 and the fluidic design 2 favorably form a common compact unit during application.

In a typical application, the upstream thermoelectric element 10a is operated as heating element for a pre-administration heating time in a range of a number of seconds prior the administration of a drug pulse and the heating favorably continues during the administration of the drug pulse. Favorably, heating is further continued for an after-administration heating time subsequent to the drug pulse administration. The after-administration heating time may, e.g. be in a range of 0.5 sec.

Further, the heating time, in particular the pre-administration heating time, may be selected in dependence of the drug pulse volume and may in particular increase with decreasing drug pulse volume. The following list gives exemplary values for the total heating time (including pre-administration heating time and after-administration heating time):

7 sec for a drug pulse volume from 100 nl up to 299 nl
6 sec for a drug pulse volume from 300 nl up to 399 nl
5 sec for a drug pulse volume from 400 nl up to 499 nl
4 sec for a drug pulse volume from 500 nl up to 599 nl
3 sec for a drug pulse volume of 600 nl or more.

The ambulatory infusion device 7 may be arranged to be carried, e.g. in a trousers' pocket, with a belt clip, or the like, and/or may be designed for direct attachment to the skin as so-called patch pump. A number of suited overall designs and architectures is known in the art.

Figure 10A:
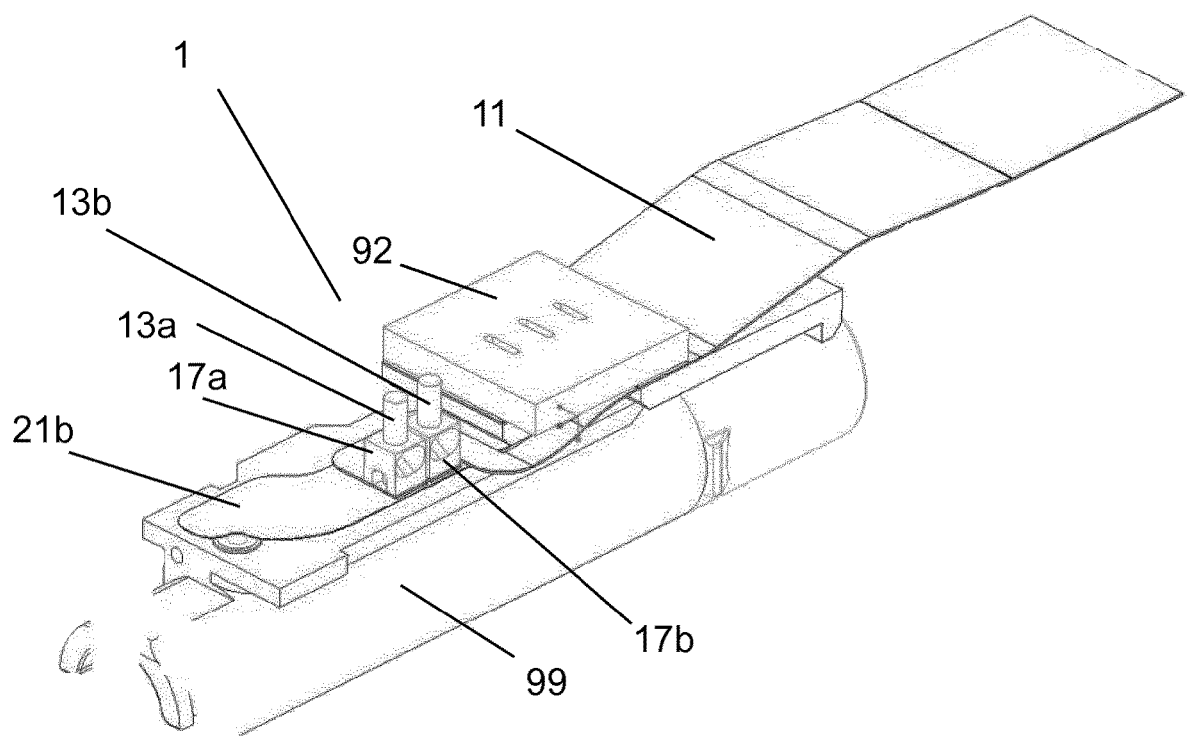
FIGS. 10a, 10b show a further embodiment of a flow detector in operative coupling with a dosing unit.
Figure 10B:
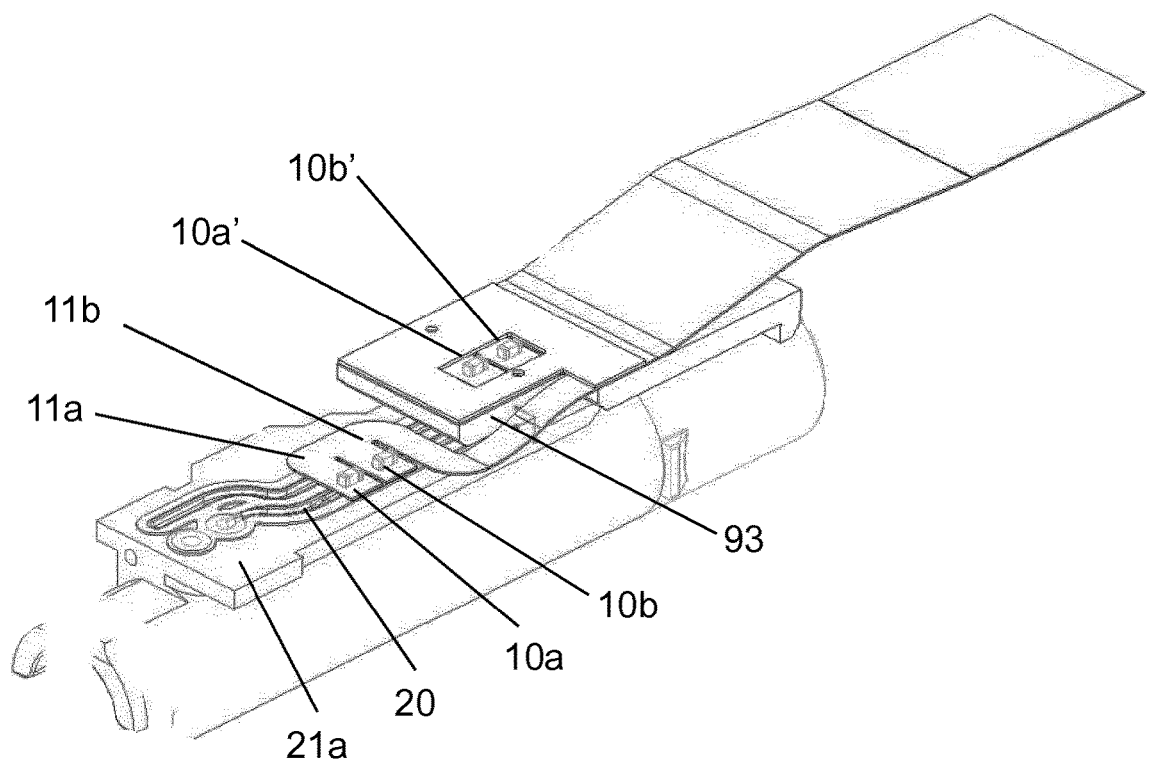

In the following, reference is additionally made to FIGS. 10a, 10b, showing a further exemplary embodiment of a flow detector 1 in accordance with the present disclosure. In this example, the flow detector 1 is shown in the context of a downstream dosing unit as mentioned before and disclosed, e.g. in EP1970677A1, EP EP2881128A1. This however, is not essential and the flow detector 1 of this type of embodiment may also be used in the context of other ambulatory infusion systems, as discussed, e.g. in the context of FIG. 9. The views of FIGS. 10a, 10b are identical, except that a number of elements is omitted as explained further below.

In FIGS. 10a, 10b, ref. 99 refers to the dosing cylinder of the downstream dosing unit. A fluidic platform 21a is provided with the dosing cylinder 99 in an integral way. The fluidic platform 21 comprises the flow channel 20 in form of a groove that is fluidic coupled with the outlet port respectively draining port of a valve (not shown) of the dosing unit and a fluidic outlet (not shown) as generally explained in the context of FIG. 9. The flow channel 20 is covered by a foil 21b (removed in FIG. 10b) of good thermal conductivity. In combination, the fluidic platform 21a and the foil 22b delimit the flow channel 20.

Regarding the arrangement and operation of the upstream thermoelectric element 10a and the downstream thermoelectric element 10b, the design of FIGS. 10a, 10b substantially corresponds to the design shown in FIGS. 2, 3 to which reference is additionally made in this regard.

The separate element carriers 11a, 11b extend from a flexible printed circuit board 11 on which also a first reference thermoelectric element 10a' and a second reference thermoelectric element 10b' are arranged. In contrast to the upstream thermoelectric element 10a and the downstream thermoelectric element 10b, the first reference thermoelectric element 10a' and the second reference thermoelectric element 10b' are thermally decoupled from the flow channel by way of a plastic insulating element 93 that is arranged between the first and second reference thermoelectric elements 10a', 10b' on the one side and the flow channel 20 respectively the foil 21b. Further, an insulating cover 92 is provided that covers the portion of the flexible circuit board 11 where the first and second reference thermoelectric element 10a', 10b' are located. The first and second reference thermoelectric element 10a', 10b' are accordingly arranged between the insulating element 93 and the insulating cover 92.

The positioning of the first and second reference thermoelectric element 10a', 10b' with respect each other favourable corresponds to the positioning of the upstream thermoelectric element 10a and the downstream thermoelectric element 10b with respect to each other. In particular, the distance between the first reference thermoelectric element 10a' and the second reference thermoelectric element 10b' corresponds to the distance between the upstream thermoelectric element 10a and the downstream thermoelectric element 10b. The insulating cover 92 is designed such that the mutual thermal coupling between the first r4ference thermoelectric element 10a' and the second reference thermoelectric element 10b' corresponds to the mutual thermal coupling between the upstream thermoelectric element 10a and the downstream thermoelectric element 10b if no flow is present in the flow channel.

It is noted that the design of FIGS. 10a, 10b does not use a middle thermoelectric element as dedicated heating element. If such middle thermoelectric element (arranged between the upstream thermoelectric element 10a and the downstream thermoelectric element 10b) is present, a third reference thermoelectric element as dedicated reference heating element is favourable also provided and arranged between the first and second reference thermoelectric element, respectively.

Figure 11:
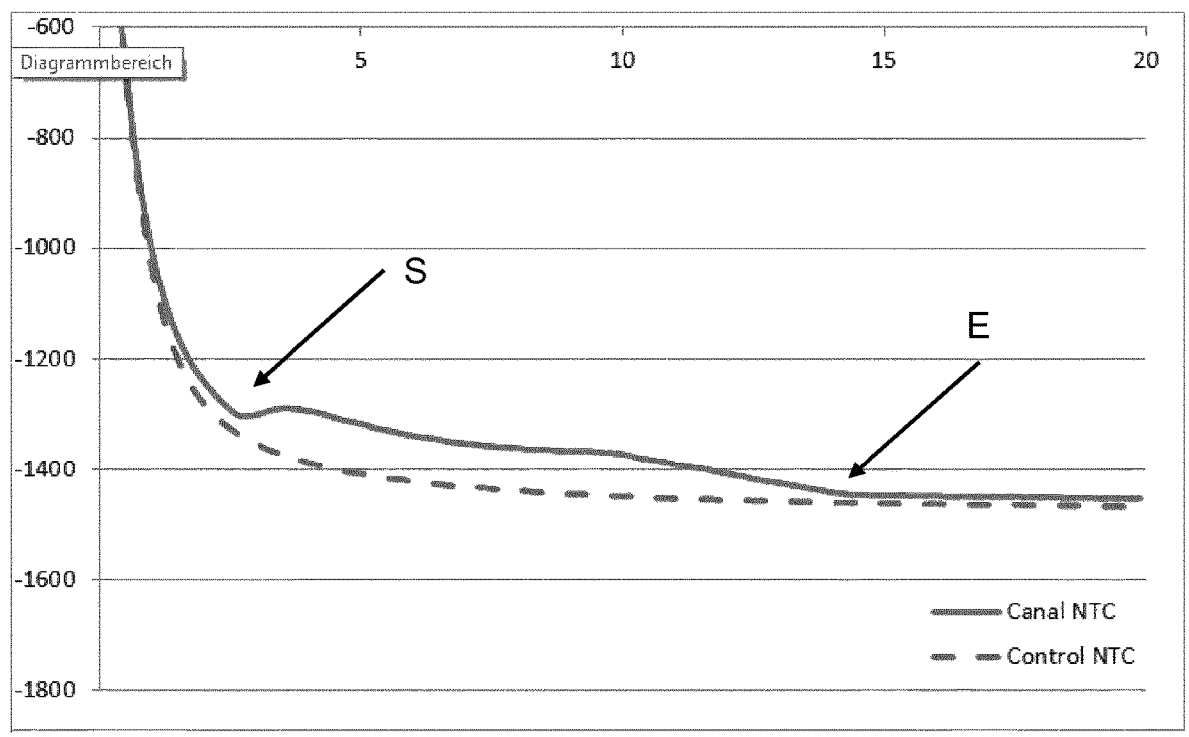
FIG. 11 shows the outputs of flow curve and a reference curve for an embodiment of a flow detector.

In the following, reference is additionally made to FIG. 11. FIG. 11 shows exemplary measurement results, similar to FIG. 8, as obtained in an arrangement with additional first and second reference thermoelectric elements 10a', 10b', as explained before with reference to FIGS. 10a, 10b. In FIG. 11, the solid curve (labelled "Canal NTC", also referred to as "flow curve") shows the measurement results based on the upstream thermoelectric element 10a and the downstream thermoelectric element 10b. The dashed curve (labelled "Control NTC", also referred to as "reference curve") shows the measurement results based on the first and second reference thermoelectric elements 10a', 10b'. The start of the liquid flow within the flow channel 20 is indicated by "S", while the end of the liquid flow is indicated by "E".

Considering the flow curve alone, it can be seen that the start and in particular the end of the liquid flow is hard to determine. It can further be seen that both curves substantially coincide before the start of the liquid flow, indicating a good correspondence. With the beginning of the liquid flow, both curves start diverging, with the reference curve not being influenced by the liquid flow, in contrast to the flow curve. Further, with the liquid flow ending, the flow curves again approaches the reference curve until both curves finally coincide again. By evaluating both curves in combination and in particular the deviation between the flow curve and the reference curve, the start and end of the liquid flow can accordingly be determined with substantially improved precision and reliability. It can be seen that at the change in flow is comparatively fast at "S", while it is slow and creeping at "E". As short flow events (e.g. the administration of volumes of less than 1 µl during administering low basal rates) always change the flow rapidly, it is sufficient to evaluate short flow events just with the thermoelectric elements 10a and 10b as explained before. Any obstructions of flow will lead to slow or no change in flow and will be detected reliably as "no flow" since a rapid flow change is expected. Larger boli are flow events of longer duration which can eventually be obstructed in a slow manner. Therefore, these long flow events are evaluated preferably with both pairs of thermoelectric elements 10a, 10b and 10a', 10b'. While the slow decrease in flow cannot be reliably detected using the upstream thermoelectric element 10a and the downstream thermoelectric element 10b alone, the creeping decrease of flow will reliably be detected by comparison with of the flow-independent signals that are generated by the reference thermoelectric elements 10a', 10b'.

Figure 12:
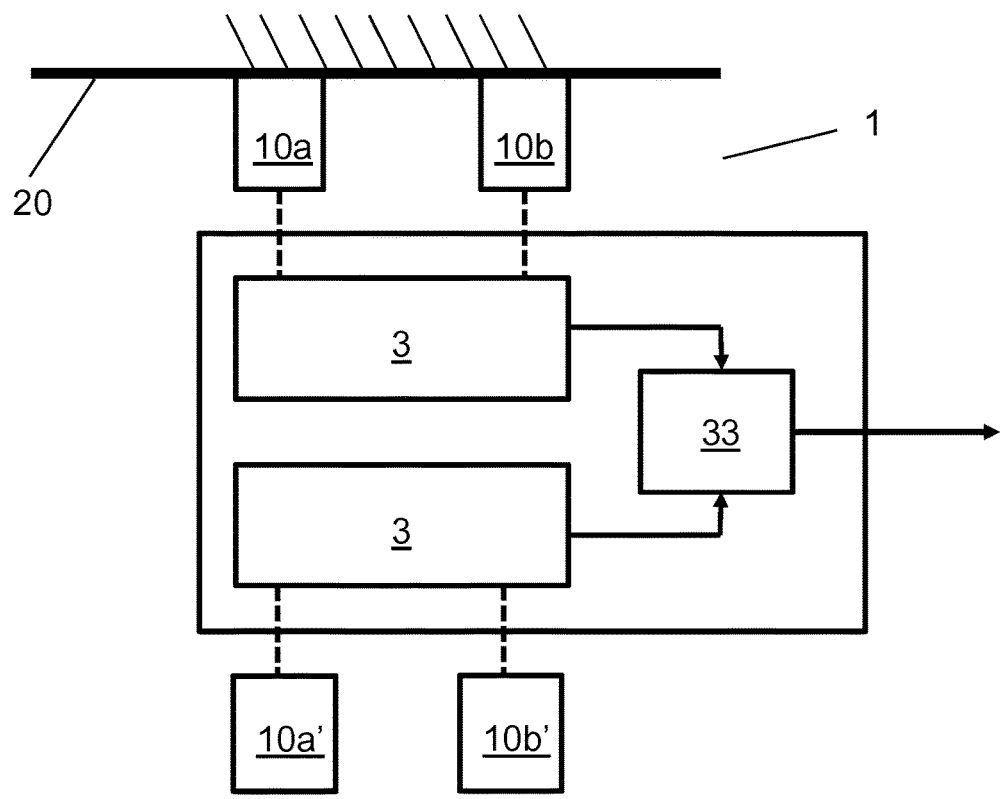
FIG. 12 shows an arrangement of a flow detector in a schematic functional view.

In the following, reference is additionally made to FIG. 12. Fig. shows an arrangement with a flow detector 1 with reference thermoelectric elements in a schematic functional view. Reference is, in this context, additionally made to FIG. 9. It can be seen that two separate evaluation units 3 are present, which may be designed according to any of the before-discussed embodiments, based, e.g. on circuitry as shown in FIG. 6 or FIG. 7. One of the two evaluation units 3 is coupled with the upstream thermoelectric element 10a and the downstream thermoelectric element 10b. The other evaluation unit 3 is coupled with the first reference thermoelectric element 10a' and the second reference thermoelectric element 10b'. Both evaluation units are independent from each other. The outputs of the two evaluation units generally corresponds to the flow curve as shown in FIG. 11. The outputs of the two evaluation units 3 are fed into an compensation unit that is exemplarily realized as difference computation unit 33 that determines the difference of the output signals provided by the two evaluation units 3. The output of the difference computation unit 33 corresponds to the difference between the flow curve and the reverence curve as explained before, indicating the actual liquid flow within the flow channel 20. The two evaluation units 3 and the difference computation unit 33 form, in combination, an evaluation and compensation unit as explained before. Optionally, it may be designed to operate in a first mode of operation or a second mode of operation as explained before.

The invention claimed is:

1. A flow detector for releasable coupling with a flow channel in a channel coupling area and detecting a flow of liquid drug in the flow channel, the flow detector including:
    an upstream thermoelectric element and a downstream thermoelectric element, wherein the upstream thermoelectric element and the downstream thermoelectric element are arranged spaced apart from each other and movable independent from each other;
    an upstream biasing element and a downstream biasing element, wherein the upstream biasing element acts on the upstream thermoelectric element, thereby biasing the upstream thermoelectric element towards the channel coupling area, and the downstream biasing element acts on the downstream thermoelectric element, thereby biasing the downstream thermoelectric element towards the channel coupling area independently from the upstream biasing element; and
    wherein the upstream thermoelectric element and the downstream thermoelectric element have an air gap therebetween to inhibit thermal conduction.

2. The flow detector according to claim 1, wherein the flow detector further includes a middle thermoelectric element, wherein the middle thermoelectric element is arranged between and spaced apart from the upstream thermoelectric element and the downstream thermoelectric element and is movable independent from the upstream thermoelectric element and the downstream thermoelectric element; and wherein the flow detector comprises a middle biasing element, wherein the middle biasing element acts on the middle thermoelectric element, thereby biasing the middle thermoelectric element towards the channel coupling area independent from the upstream biasing element and the downstream biasing element.

3. An ambulatory infusion device, including:
a fluidic device coupler, the fluidic device coupler being designed for releasable mating coupling, in an operational configuration, with an infusion device coupler of a fluidic device with a flow channel;
a pump drive unit, configured to administer liquid drug out of a drug container to a patient's body via the flow channel;
a pump control unit, configured to control operation of the pump drive unit for continuous drug administration according to a time-variable basal infusion administration rate;
the flow detector according to claim 1 in operative coupling with the pump control unit.

4. The ambulatory infusion device according to claim 3, wherein the pump control unit is configured to control the pump drive unit to administer drug pulses of pre-set pulse volume and to vary a time between consecutive pulses in dependence of a required basal administration rate, and wherein the flow detector is configured to be intermittently operated for administration of the drug pulses.

5. The flow detector according to claim 1, wherein the upstream thermoelectric element and the downstream thermoelectric element are configured to contact an exterior wall of the flow channel.

6. The flow detector according to claim 5, wherein the upstream thermoelectric element is configured to operate as a heating element to heat the liquid drug in the flow channel via conduction through the exterior wall of the flow channel.

7. A flow detector for releasable coupling with a flow channel in a channel coupling area and detecting a flow of liquid drug in the flow channel, the flow detector including:
an upstream thermoelectric element and a downstream thermoelectric element, wherein the upstream thermoelectric element and the downstream thermoelectric element are arranged spaced apart from each other, and wherein the upstream thermoelectric element is arranged to couple to the flow channel in the channel coupling area at an upstream position and the downstream thermoelectric element is arranged to releasably couple to the flow channel in the channel coupling area at a downstream position, such that the downstream thermoelectric element operates as a downstream temperature sensor and senses a downstream temperature at the downstream position;
wherein the upstream thermoelectric element is configured to operate as a heating element, thereby heating liquid inside the flow channel at the upstream position, and operate as an upstream temperature sensor and sense an upstream temperature at the upstream position;
wherein the upstream thermoelectric element is arranged on an upstream flexible printed circuit board element;
wherein the downstream thermoelectric element is mounted on a downstream flexible printed circuit board element; and
wherein the upstream flexible printed circuit board element and the downstream flexible printed circuit board element form fingers that are able to flex independently from one another.

8. The flow detector according to claim 7, the flow detector further including a first reference thermoelectric element and a second reference thermoelectric element, the first reference thermoelectric element and the second reference thermoelectric element being arranged in a thermal isolated manner with respect to the flow channel.

9. The flow detector according to claim 7, wherein the upstream thermoelectric element is arranged on an upstream element carrier and the downstream thermoelectric element is arranged on a downstream element carrier, and a gap is present between the upstream element carrier and the downstream element carrier.

10. The flow detector according to claim 7, wherein the flow detector includes a positioning structure, the positioning structure being designed to position the flow channel with respect to the upstream thermoelectric element and the downstream thermoelectric element.

11. The flow detector according to claim 7, wherein the upstream thermoelectric element and the downstream thermoelectric element are thermistors, in particular negative temperature coefficient (NTC) thermistors.

12. The flow detector according to claim 11, wherein the upstream thermoelectric element and the downstream thermoelectric element are NTC thermistors of different electric resistance.

13. The flow detector according to claim 7, wherein the flow detector includes an evaluation unit, wherein the evaluation unit is designed to provide an output signal of variable frequency, wherein the frequency depends on a difference between the upstream temperature as sensed by the upstream thermoelectric element and the downstream temperature as sensed by the downstream thermoelectric element.

14. The flow detector according to claim 7, wherein a gap is present between the upstream flexible printed circuit board element and the downstream flexible printed circuit board element, and wherein the gap is an air gap between the upstream flexible printed circuit board element and the downstream flexible printed circuit board element to inhibit thermal conduction therebetween.

15. A method for releasably coupling a flow detector with a flow channel for detecting a flow of liquid drug in the flow channel, the method including:
releasably coupling an upstream thermoelectric element and a downstream thermoelectric element with the flow channel, wherein the upstream thermoelectric element and the downstream thermoelectric element are arranged spaced apart from each other along an extension direction of the flow channel and movable independent from each other;
biasing the upstream thermoelectric element towards the flow channel, and independently biasing the downstream thermoelectric element towards the flow channel, wherein the biasing the upstream thermoelectric element includes pressing the upstream thermoelectric element against an exterior wall of the flow channel; and
heating the liquid drug in the flow channel by conducting heat from the upstream thermoelectric element through the exterior wall of the flow channel.

16. The method according to claim 15, the method further including providing a first reference thermoelectric element and a second reference thermoelectric element, the first reference thermoelectric element and the second reference thermoelectric element being arranged in a thermal isolated manner with respect to the flow channel, the method further including:
determining a flow-dependent output signal by processing a signal provided by the upstream thermoelectric element and the downstream thermoelectric element;
independently determining a reference output signal by processing a signal provided by the first reference thermoelectric element and the second reference thermoelectric element;

evaluating a relation between the flow-dependent output signal and the reference output signal.

\* \* \* \* \*